US012119099B2

(12) United States Patent
Cowan et al.

(10) Patent No.: US 12,119,099 B2
(45) Date of Patent: Oct. 15, 2024

(54) SYSTEM FOR CONDUCTING A FLUID INJECTION PROCEDURE

(71) Applicant: BAYER HEALTHCARE LLC, Whippany, NJ (US)

(72) Inventors: Kevin Cowan, Allison Park, PA (US); Edward Liscio, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 867 days.

(21) Appl. No.: 17/270,886

(22) PCT Filed: Sep. 10, 2019

(86) PCT No.: PCT/US2019/050296
§ 371 (c)(1),
(2) Date: Feb. 24, 2021

(87) PCT Pub. No.: WO2020/055788
PCT Pub. Date: Mar. 19, 2020

(65) Prior Publication Data
US 2021/0193289 A1    Jun. 24, 2021

Related U.S. Application Data

(60) Provisional application No. 62/730,204, filed on Sep. 12, 2018.

(51) Int. Cl.
*B65B 3/00* (2006.01)
*B65B 57/14* (2006.01)
(Continued)

(52) U.S. Cl.
CPC ............. *G16H 20/17* (2018.01); *B65B 3/003* (2013.01); *B65B 57/145* (2013.01); *G16H 10/60* (2018.01);
(Continued)

(58) Field of Classification Search
CPC .............................. B65B 3/003; B65B 57/145
See application file for complete search history.

(56) References Cited

U.S. PATENT DOCUMENTS 766,169 A    8/1904  Christiansen
5,383,858 A  1/1995  Reilly et al.
(Continued)

FOREIGN PATENT DOCUMENTS

EP    3057648 A1       8/2016
EP    3057648 B1  *  11/2018  ............ A61M 5/007
(Continued)

OTHER PUBLICATIONS

"International Preliminary Report on Patentability from PCT Application No. PCT/US2019/050296", Mar. 25, 2021.

*Primary Examiner* — Stephen F. Gerrity
(74) *Attorney, Agent, or Firm* — James R. Stevenson; Ryan Miller

(57) ABSTRACT

A system for conducting a fluid injection procedure comprises: a loading device for filling containers with fluid; an information read/write device operatively associated with the loading device and configured to: read information related to the containers stored on information storage devices associated with the containers and write information related to an injection procedure and/or a patient to the information storage devices; and a fluid injector system configured to receive the containers after filling by the loading device and inject the contents of the containers of fluid into the patient. The loading device is configured to fill the containers with fluid based on the information related to the containers read from the information storage devices. The information read/write device is configured to write information to the information storage device. The fluid
(Continued)

injector system is configured to read the information and use this information to program the fluid injector system.

22 Claims, 18 Drawing Sheets

(51) Int. Cl.
    *G16H 10/60*     (2018.01)
    *G16H 20/17*     (2018.01)
    *G16H 40/67*     (2018.01)

(52) U.S. Cl.
    CPC .......... *G16H 40/67* (2018.01); *A61J 2205/10* (2013.01); *A61J 2205/60* (2013.01)

(56) References Cited

U.S. PATENT DOCUMENTS

| | | |
|---|---|---|
| 7,553,294 B2 | 6/2009 | Lazzaro et al. |
| 7,666,169 B2 | 2/2010 | Cowan et al. |
| 9,173,955 B2 | 11/2015 | Ryall |
| 9,173,995 B1 | 11/2015 | Tucker et al. |
| 9,199,033 B1 | 12/2015 | Cowan et al. |
| 9,474,857 B2 | 10/2016 | Riley et al. |
| 2004/0182475 A1* | 9/2004 | Vetter et al. ............ B65B 3/003 141/311 R |
| 2008/0033368 A1* | 2/2008 | Fago ...................... G16H 20/13 604/189 |
| 2010/0174180 A1* | 7/2010 | Rousso et al. .......... G16H 30/40 600/431 |
| 2010/0305506 A1* | 12/2010 | Fahrer ............... A61M 5/14546 604/118 |
| 2011/0061765 A1* | 3/2011 | Hartman et al. ........ B65B 3/003 141/2 |
| 2011/0137162 A1* | 6/2011 | Bruce et al. ...... A61M 5/14546 600/432 |
| 2012/0035472 A1* | 2/2012 | Bruce et al. ...... A61M 5/14546 600/432 |
| 2014/0027009 A1 | 1/2014 | Riley et al. |
| 2015/0126961 A1 | 5/2015 | Laugere et al. |
| 2015/0127376 A1* | 5/2015 | Ortenzi et al. ......... A61M 5/007 705/3 |
| 2017/0033619 A1 | 2/2017 | Tamura |
| 2017/0035974 A1 | 2/2017 | Berry et al. |
| 2017/0056603 A1 | 3/2017 | Cowan et al. |
| 2017/0112995 A1 | 4/2017 | Sams et al. |
| 2017/0333624 A1 | 11/2017 | Tucker et al. |
| 2018/0161496 A1 | 6/2018 | Berry et al. |
| 2020/0390965 A1 | 12/2020 | Langseth-Manrique et al. |

FOREIGN PATENT DOCUMENTS

| | | |
|---|---|---|
| WO | 2006108026 A2 | 10/2006 |
| WO | 2010014654 A1 | 2/2010 |
| WO | 2010117918 A1 | 10/2010 |
| WO | 2015164783 A1 | 10/2015 |
| WO | 2016112163 A1 | 7/2016 |
| WO | 2016172467 A1 | 10/2016 |
| WO | 2016191485 A1 | 12/2016 |
| WO | 2018075386 A1 | 4/2018 |
| WO | 2019055497 A1 | 3/2019 |
| WO | 2020055785 A1 | 3/2020 |
| WO | 2020055788 A1 | 3/2020 |

\* cited by examiner

SYSTEM FOR CONDUCTING A FLUID INJECTION PROCEDURE

CROSS REFERENCE TO RELATED APPLICATIONS

This application is a § 371 U.S. national phase application of International Patent Application No. PCT/US2019/050296, filed Sep. 10, 2019, and claims priority to U.S Provisional Patent Application Ser. No. 62/730,204, entitled "Systems for Conducting a Fluid Injection Procedure", filed Sep. 12, 2018, the contents of which are incorporated herein by reference.

BACKGROUND OF THE DISCLOSURE

Field

The present disclosure relates to systems, devices, and/or methods for performing an injection procedure by which fluid(s) in one or more containers are to be administered via a fluid injection system to a patient as part of an imaging procedure.

Description of Related Art

Contrast media are administered to patients to enhance the contrast of bodily structures or fluids during certain medical procedures. For example, contrast media are used in diagnostic imaging procedures, including X-ray, computed tomography (CT), magnetic resonance imaging (MRI), and ultrasound, and in interventional radiological procedures, such as angioplasty and certain types of chemotherapy. Various forms and concentrations of contrast media are available and are selected based on the type of procedure and the subject of interest. Illustrative contrast media include barium- and iodine-based solutions commonly used in radiological imaging procedures. Contrast media may be delivered to patients through various methods, including ingestion, manual injections, or automated fluid delivery systems.

In many medical diagnostic and therapeutic procedures, a physician or other person injects a patient with a fluid. In recent years, a number of injector-actuated syringes and fluid injectors for pressurized injection of medical fluids, such as a contrast solution (often referred to simply as "contrast"), a flushing agent, such as saline, and other medical fluids, have been developed for use in procedures such as angiography, computed tomography (CT), ultrasound, magnetic resonance imaging (MRI), positron emission tomography (PET), and molecular imaging procedures. In general, these fluid injectors are designed to deliver a preset amount of fluid at a preset pressure and/or flow rate.

Typically, such powered injectors include a housing allowing one or more syringes to be connected to a front wall thereof. These injectors usually comprise one or two drive members each of which typically featuring a piston that connects to a syringe plunger. A syringe used with a front-loading injector usually includes a readily releasable mounting mechanism for securing the syringe to the front wall of the injector. Such syringes may, for example, include a syringe body, a plunger reciprocally mounted therein, and a plunger extension for transfer of force to the plunger.

Such syringes are typically purchased either in a "prefilled" state, containing injection fluid supplied by the manufacturer, or in an empty, "fillable" state. Under current practice, empty syringes are typically attached to or loaded onto the powered injector (either directly or via an adapter as known in the art) and connected via tubing to a source of injection fluid such as a bag or a bottle. The drive member of the powered injector is then reversed to draw the syringe plunger rearward within the syringe, thereby drawing injection fluid from the source into the syringe for later injection into a patient. Thereafter, the powered injector is programmed with the applicable parameters to carry out the appropriate medical procedure. In many medical applications, however, powered injectors are used in procedures and areas in which there are substantial time and access constraints. In time and/or access constrained procedures, the loading of injection fluid into empty syringes using a powered injector and then programming the powered injector to carry out the appropriate fluid injection procedure, results in inefficient use of personnel, equipment, time and/or space.

It is, therefore, desirable to develop improved syringe loading/filling devices, improved systems and methods for programming powered injectors, and systems and methods to improve the efficiency of use of personnel, equipment, time and/or space.

SUMMARY

In accordance with one aspect of the present disclosure, provided is a system for conducting a fluid injection procedure. The system comprises: (a) a container loading system comprising a loading device for filling one or more containers with fluid; (b) an information read/write device operatively associated with the loading device and configured to: read information related to the one or more containers stored on one or more information storage devices associated with the one or more containers; and write information related to at least one of an injection procedure and a patient to the one or more information storage devices; and (c) a fluid injector system configured to receive the one or more containers after filling by the container loading system and inject contents of the one or more containers of fluid into the patient. The loading device is configured to fill the one or more containers with fluid based on the information related to the one or more containers read from the one or more information storage devices by the information read/write device. The information read/write device is configured to write the information related to at least one of the injection procedure and the patient to the information storage device as the loading device is filling the one or more containers with fluid. The fluid injector system is configured to read the information related to at least one of the injection procedure and the patient from the one or more information storage devices when the one or more containers are received by the fluid injector system and the information related to at least one of the injection procedure and the patient is used to program the fluid injector system to conduct the injector procedure.

In some non-limiting embodiments or aspects, the one or more containers of fluid may include a container of contrast media and a container of saline. The container of contrast media and the container of saline may be coupled together via a collar. The one or more information storage devices may be provided on the collar. The removal of the collar from the container of contrast media and the container of saline removes information stored on the one or more information storage devices, thereby allowing the collar to be reused. Alternatively, the container of contrast media and the container of saline may be coupled together via a faceplate. The faceplate may be configured to removably engage both the container loading system and the fluid injector system. The one or more information storage devices may be provided in the faceplate. In addition, the faceplate may include a display device for displaying at least one of: information regarding the patient or information regarding a fluid injection procedure.

In other non-limiting embodiments or aspects, the information related to the one or more containers stored on the one or more information storage devices may comprise at least one of the following items: (i) a type of the contrast media, (ii) a concentration of the contrast media, (iii) a manufacturer of the contrast media, (iv) a lot number of the contrast media, (v) a serial number of the contrast media, (vi) a manufacturer instructions for the contrast media, (vii) a creation date of the contrast media, (viii) an expiration date of the contrast media, and (ix) a size of the one or more containers. The information related to the one or more containers stored on the one or more information storage devices may be generated by the manufacturer or supplier of the fluid contained in the one or more containers. The information related to at least one of the injection procedure and the patient written to the one or more information storage devices may include at least one of: (i) a pressure and a flow rate to be used by the fluid injector system, (ii) patient weight information, (iii) patient height information, (iv) patient age information, (v) patient name information, (vi) hospital information, (vii) department information, (viii) doctor information, (ix) medical procedure information, (x) medical imaging information, and (xi) automated injection information.

In still other non-limiting embodiments or aspects, the information read/write device may be an RFID read/write device and the one or more information storage devices are RFID tags. Alternatively, the information read/write device may be a barcode reader and a barcode printer and the one or more information storage devices are barcode labels. The barcode reader may be configured to read information related to the one or more containers stored on one or more bar code labels associated with the one or more containers; and the barcode printer may be configured to print bar code labels including information related to at least one of the injection procedure and the patient.

In accordance with another aspect of the present disclosure, provided is a system for conducting a fluid injection procedure. The system comprises: (a) a container loading system comprising a loading device for filling one or more containers with fluid; (b) a data entry system associated with the loading device and configured to allow entry of at least one of information related to the one or more containers; information related to at least one of an injection procedure; and information related to a patient; (c) a controller operatively connected to the loading device and the data entry system and configured to receive at least one of the information related to the one or more containers; the information related to at least one of the injection procedure; and the information related to the patient and associate at least one of the information related to the one or more containers; the information related to at least one of the injection procedure; and the information related to the patient with the one or more containers as the loading device is filling the one or more containers with fluid; (d) a communication device operatively connected to the controller and configured to transmit at least one of the information related to the one or more containers; the information related to at least one of the injection procedure; and the information related to the patient; and (e) a fluid injector system configured to: receive at least one of the information related to the one or more containers; the information related to at least one of the injection procedure; and the information related to the patient from the communication device; and associate at least one of the information related to the one or more containers; the information related to at least one of the injection procedure; and the information related to the patient with the one or more containers when the one or more containers are mounted to the fluid injector system.

In some non-limiting embodiments or aspects, at least one of the information related to the one or more containers, the information related to at least one of the injection procedure, and the information related to the patient is associated with the one or more containers as the loading device is filling the one or more containers with fluid by at least one of: (i) assigning the one or more containers with a unique code that can be entered into the fluid injector system, and (ii) storing at least one of the information related to the one or more containers, the information related to at least one of the injection procedure, and the information related to the patient on a data storage device provided on the one or more container. The data storage device may be one of an RFID tag and a barcode label.

In other non-limiting embodiments or aspects, the information related to the one or more containers may comprise at least one of the following items: (i) a type of the contrast media, (ii) a concentration of the contrast media, (iii) a manufacturer of the contrast media, (iv) a lot number of the contrast media, (v) a serial number of the contrast media, (vi) a manufacturer instructions for the contrast media, (vii) a creation date of the contrast media, (viii) an expiration date of the contrast media, and (ix) a size of the one or more containers. The information related to the one or more containers may be generated by the manufacturer or supplier of the fluid contained in the one or more containers. In addition, the information related to the injection procedure and information related to the patient may comprises at least one of: (i) a pressure and a flow rate for the fluid injector system, (ii) patient weight information, (iii) patient height information, (iv) patient age information, (v) patient name information, (vi) hospital information, (vii) department information, (viii) doctor information, (ix) medical procedure information, (x) medical imaging information, and (xi) automated injection information In still other non-limiting embodiments or aspects, the one or more containers of fluid may include a container of contrast media and a container of saline. The communication device may comprise a communication port configured to provide one or more communication methods selected from the group consisting of: Ethernet, wireless protocols, serial, universal serial bus (USB), parallel port, and Bluetooth. The communication device may be configured to transmit at least one of (i) the information related to the one or more containers, (ii) the information related to at least one of the injection procedure, and (iii) the information related to the patient to one or more of: (A) a personal computing device, (B) a server, (C) a distributed computing system, (D) a mobile computing device, (E) a picture archiving and communication system (PACS), (F) a healthcare information and management systems (HIMS), (G) an electronic medical record (EMR) system, (H) a radiology information system (RIS), and (I) a contrast information management system.

In accordance with some examples or aspects, the disclosure of the present application may be characterized by one or more of the following numbered clauses:

Clause 1: A system for conducting a fluid injection procedure, the system comprising: (a) a container loading system comprising a loading device for filling one or more containers with fluid; (b) an information read/write device operatively associated with the loading device and configured to: read information related to the one or more containers stored on one or more information storage devices associated with the one or more containers; and write information related to at least one of an injection procedure and a patient to the one or more information storage devices; and (c) a fluid injector system configured to receive the one or more containers after filling by the container loading system and inject contents of the one or more containers of fluid into the patient, wherein (i) the loading device is configured to fill the one or more containers with fluid based on the information related to the one or more containers read from the one or more information storage devices by the information read/write device; (ii) the information read/write device is configured to write the information related to at least one of the injection procedure and the patient to the information storage device as the loading device is filling the one or more containers with fluid; and (iii) the fluid injector system is configured to read the information related to at least one of the injection procedure and the patient from the one or more information storage devices when the one or more containers are received by the fluid injector system and the information related to at least one of the injection procedure and the patient is used to program the fluid injector system to conduct the injector procedure.

Clause 2: The system of clause 1, wherein the one or more containers of fluid includes a container of contrast media and a container of saline.

Clause 3: The system of clause 2, wherein the container of contrast media and the container of saline are coupled together via a collar.

Clause 4: The system of clause 2 or clause 3, wherein the one or more information storage devices are provided on the collar.

Clause 5: The system of clauses 2-4, wherein removal of the collar from the container of contrast media and the container of saline removes information stored on the one or more information storage devices, thereby allowing the collar to be reused.

Clause 6: The system of clause 2, wherein the container of contrast media and the container of saline are coupled together via a faceplate.

Clause 7: The system of clause 2 or clause 6, wherein the faceplate is configured to removably engage both the container loading system and the fluid injector system.

Clause 8: The system of clause 2, clause 6, or clause 7, wherein the one or more information storage devices are provided in the faceplate.

Clause 9: The system of clause 2 or clauses 6-8, wherein the faceplate comprises a display device for displaying at least one of: information regarding the patient or information regarding a fluid injection procedure.

Clause 10: The system of clauses 1-9, wherein the information read/write device is an RFID read/write device and the one or more information storage devices are RFID tags.

Clause 11: The system of clauses 1-10, wherein the information related to the one or more containers stored on the one or more information storage devices comprises at least one of the following items: (i) a type of the contrast media; (ii) a concentration of the contrast media; (iii) a manufacturer of the contrast media; (iv) a lot number of the contrast media; (v) a serial number of the contrast media; (vi) a manufacturer instructions for the contrast media; (vii) a creation date of the contrast media; (viii) an expiration date of the contrast media; and (ix) a size of the one or more containers.

Clause 12: The system of clause 11, wherein the information related to the one or more containers stored on the one or more information storage devices is generated by the manufacturer or supplier of the fluid contained in the one or more containers.

Clause 13: The system of clauses 1-12, wherein the information related to at least one of the injection procedure and the patient written to the one or more information storage devices comprises at least one of: (i) a pressure and a flow rate to be used by the fluid injector system; (ii) patient weight information; (iii) patient height information; (iv) patient age information; (v) patient name information; (vi) hospital information; (vii) department information; (viii) doctor information; (ix) medical procedure information; (x) medical imaging information; and (xi) automated injection information.

Clause 14: The system of clauses 1-13, wherein the information read/write device is a barcode reader and a barcode printer and the one or more information storage devices are barcode labels.

Clause 15: The system of clause 14, wherein the barcode reader reads information related to the one or more containers stored on one or more bar code labels associated with the one or more containers; and the barcode printer prints bar code labels including information related to at least one of the injection procedure and the patient.

Clause 16: A system for conducting a fluid injection procedure, the system comprising: (a) a container loading system comprising a loading device for filling one or more containers with fluid; (b) a data entry system associated with the loading device and configured to allow entry of at least one of information related to the one or more containers; information related to at least one of an injection procedure; and information related to a patient; (c) a controller operatively connected to the loading device and the data entry system and configured to receive at least one of the information related to the one or more containers; the information related to at least one of the injection procedure; and the information related to the patient and associate at least one of the information related to the one or more containers; the information related to at least one of the injection procedure; and the information related to the patient with the one or more containers as the loading device is filling the one or more containers with fluid; (d) a communication device operatively connected to the controller and configured to transmit at least one of the information related to the one or more containers; the information related to at least one of the injection procedure; and the information related to the patient; and (e) a fluid injector system configured to: receive at least one of the information related to the one or more containers; the information related to at least one of the injection procedure; and the information related to the patient from the communication device; and associate at least one of the information related to the one or more containers; the information related to at least one of the injection procedure; and the information related to the patient with the one or more containers when the one or more containers are mounted to the fluid injector system.

Clause 17: The system of clause 16, wherein at least one of the information related to the one or more containers; the information related to at least one of the injection procedure; and the information related to the patient is associated with the one or more containers as the loading device is filling the one or more containers with fluid by at least one of: assigning the one or more containers with a unique code that can be entered into the fluid injector system; and storing at least one of the information related to the one or more containers; the information related to at least one of the injection procedure; and the information related to the patient on a data storage device provided on the one or more container.

Clause 18: The system of clause 17, wherein the data storage device is one of an RFID tag and a barcode label.

Clause 19: The system of clauses 16-18, wherein the information related to the one or more containers comprises at least one of the following items: (i) a type of the contrast media; (ii) a concentration of the contrast media; (iii) a manufacturer of the contrast media; (iv) a lot number of the contrast media; (v) a serial number of the contrast media; (vi) a manufacturer instructions for the contrast media; (vii) a creation date of the contrast media; (viii) an expiration date of the contrast media; and (ix) a size of the one or more containers.

Clause 20: The system of clause 19, wherein the information related to the one or more containers is generated by the manufacturer or supplier of the fluid contained in the one or more containers.

Clause 21: The system of clauses 16-20, wherein the information related to the injection procedure and information related to the patient comprises at least one of: (i) a pressure and a flow rate for the fluid injector system; (ii) patient weight information; (iii) patient height information; (iv) patient age information; (v) patient name information; (vi) hospital information; (vii) department information; (viii) doctor information; (ix) medical procedure information; (x) medical imaging information; and (xi) automated injection information.

Clause 22: The system of clauses 16-21, wherein the one or more containers of fluid includes a container of contrast media and a container of saline.

Clause 23: The system of clauses 16-22, wherein the communication device comprises a communication port configured to provide one or more communication methods selected from the group consisting of: Ethernet, wireless protocols, serial, universal serial bus (USB), parallel port, and Bluetooth.

Clause 24: The system of clauses 16-23, wherein the communication device is configured to transmit at least one of the information related to the one or more containers; the information related to at least one of the injection procedure; and the information related to the patient to one or more of: a personal computing device; a server; a distributed computing system; a mobile computing device; a picture archiving and communication system (PACS); a healthcare information and management systems (HIMS); an electronic medical record (EMR) system; a radiology information system (RIS); and a contrast information management system.

These and other features and characteristics of the device of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the device of the present disclosure.

As used in the specification and the claims, the singular form of "a", "an", and "the" include plural referents unless the context clearly dictates otherwise.

DETAILED DESCRIPTION

Figure 1A:
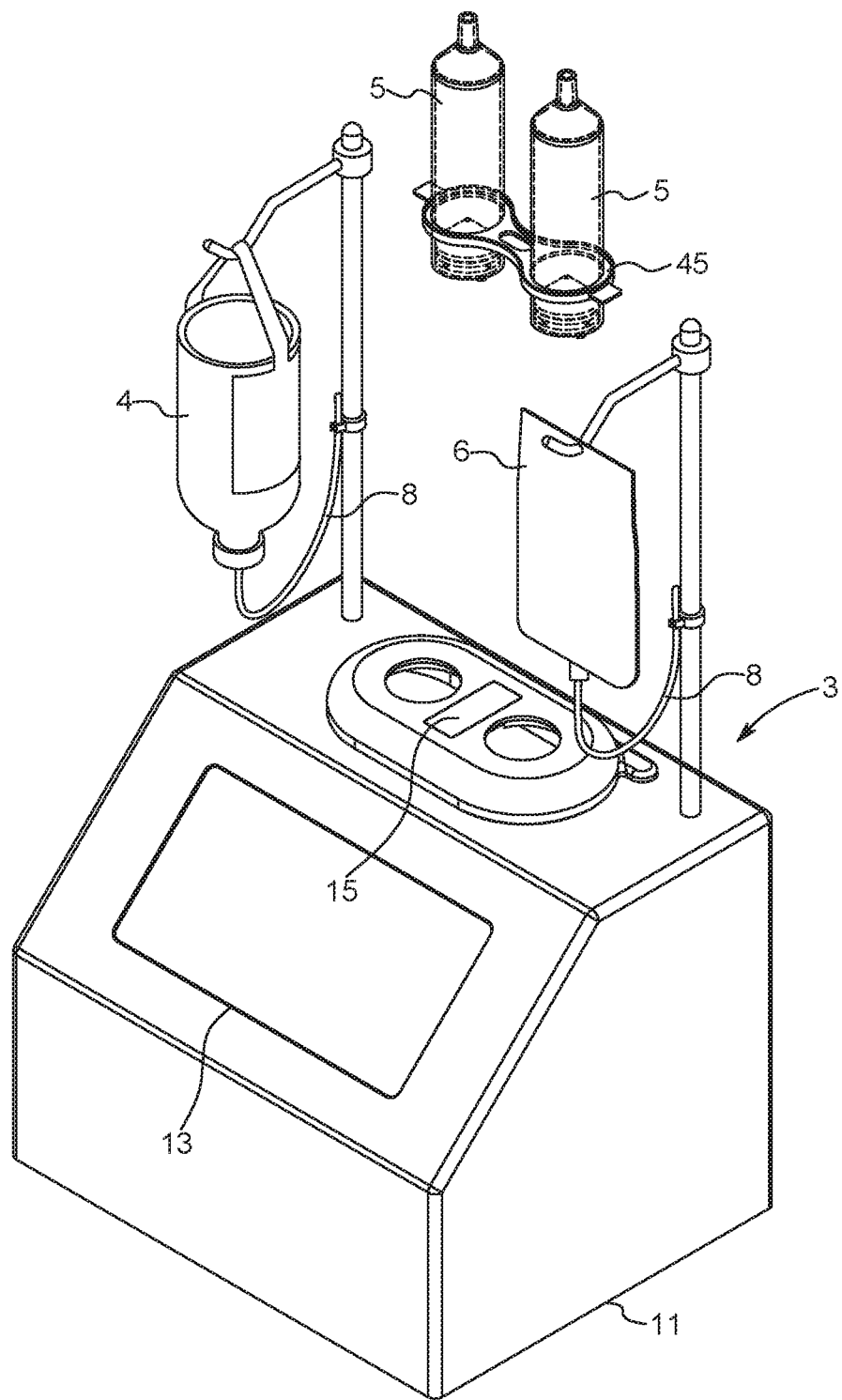
FIGS. 1A-1C are front views of a container loading device in accordance with the present disclosure during various stages of a syringe loading procedure.

For purposes of the description hereinafter, the terms "upper", "lower", "right", "left", "vertical", "horizontal", "top", "bottom", "lateral", "longitudinal", and derivatives thereof, shall relate to the device of the present disclosure as it is oriented in the drawing figures. However, it is to be understood that the device of the present disclosure may assume various alternative variations, except where expressly specified to the contrary. It is also to be understood that the specific devices illustrated in the attached drawings, and described in the following specification, are simply exemplary embodiments of the device of the present disclosure. Hence, specific dimensions and other physical characteristics related to the embodiments disclosed herein are not to be considered as limiting.

As used herein, the terms "communication" and "communicate" refer to the receipt or transfer of one or more signals, messages, commands, or other type of data. For one unit or device to be in communication with one or more other unit or device means that the one unit or device is able to receive data from and/or transmit data to the one or more other unit or device. A communication may use a direct or indirect connection, and may be wired and/or wireless in nature. Additionally, two or more units or devices may be in communication with each other even though the data transmitted may be modified, processed, routed, etc., between the first and second unit or device. For example, a first unit may be in communication with a second unit even though the first unit passively receives data and does not actively transmit data to the second unit. As another example, a first unit may be in communication with a second unit if an intermediary unit processes data from one unit and transmits processed data to the second unit. In non-limiting examples, a communication may occur through one or more wired or wireless connections, such as, through one or more wires, through direct wireless protocols such as Bluetooth, Near Field Communication (NFC), or other radio frequency protocols, and/or through indirect wireless communication such as through a local Wi-Fi network or secure Internet connection. Wireless communication may include, but is not limited to, any communication that does not require direct wired contact between the two communicating units or devices such as via a Wi-Fi network, communication via Bluetooth, NFC, or other conventional wireless system, or other non-wired electromagnetic communication systems. It will be appreciated that numerous other arrangements are possible.

The present disclosure relates a fluid injection system including a loading system and a fluid injector. The loading system is for use in loading contrast media and diluent, such as saline, into separate syringes prior to installation of those syringes in the fluid injector via which the injection procedure is to be performed as part of a contrast enhanced imaging procedure. The loading system is capable of writing to one or more information storage devices associated with the syringes on which information pertaining to the syringes, the contrast media and/or diluent therein, the injection procedure, and the patient is to be stored. The fluid injector may be configured as a dual syringe fluid injection system that, upon receiving the syringes, is capable of reading from the one or more information storage devices associated with those syringes the information pertaining to the syringes, the contrast media and/or diluent therein, the injection procedure, and the patient and using such information to program the dual syringe fluid injection system to permit the injection procedure to be performed on the patient.

Figure 1B:
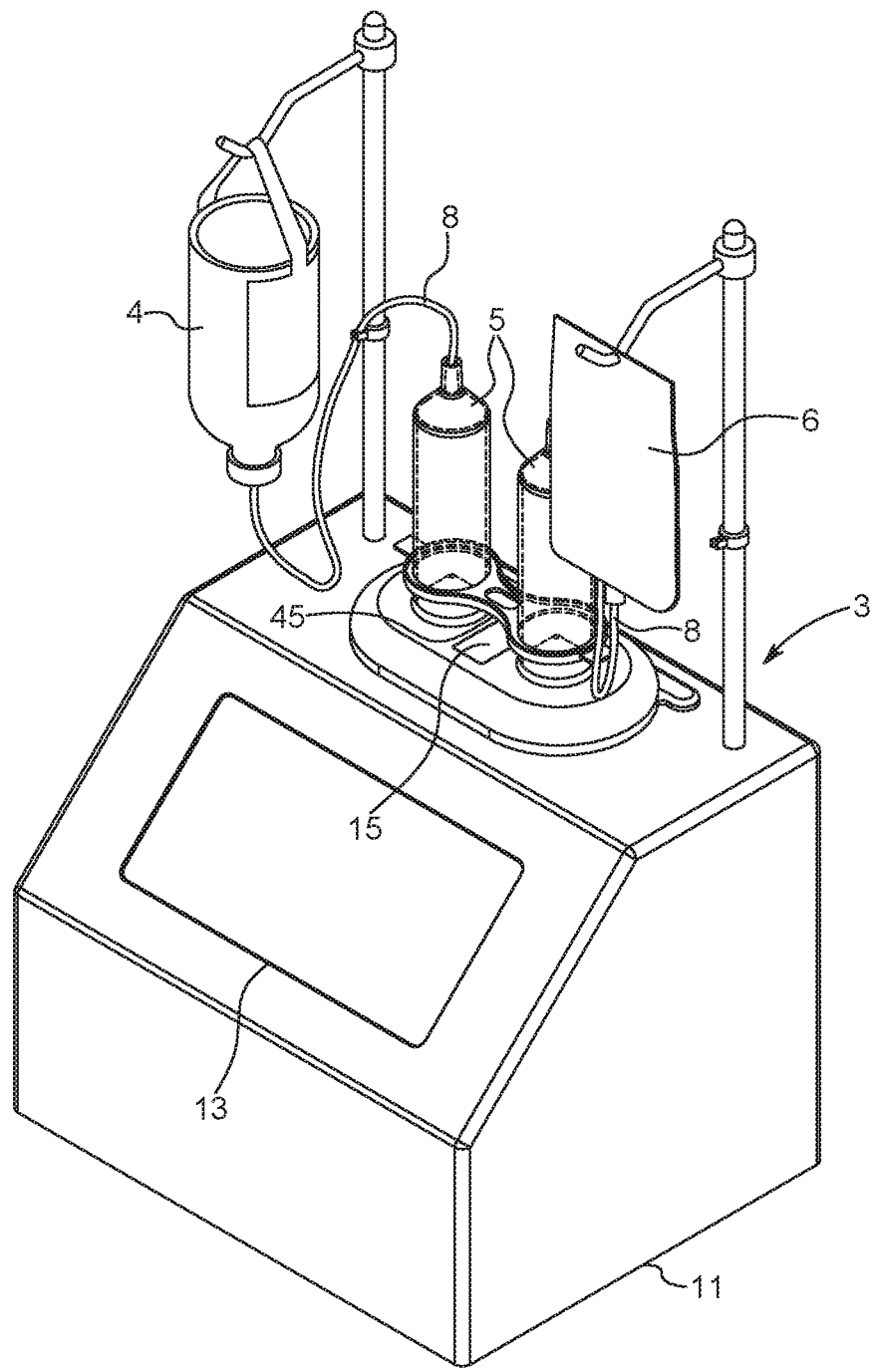
Figure 1C:
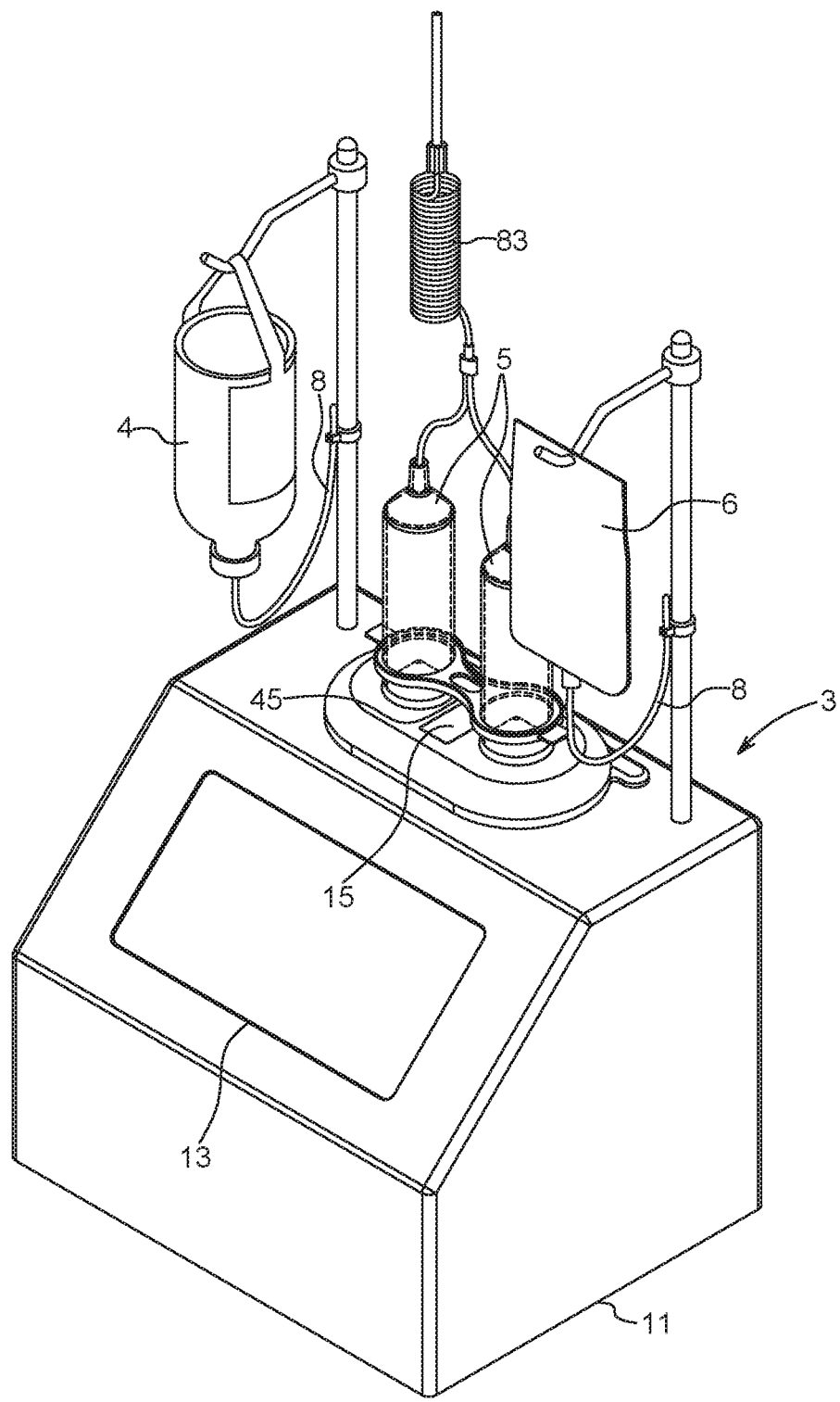

More specifically, FIGS. 1A-1C depict an illustrative container loading device 3 according to some embodiments. As shown in FIGS. 1A-1C, the container loading device 3 is configured to fill one or more containers, such as syringes 5, with a fluid, such as contrast or saline, from a bulk fluid source 4, 6. The container loading device 3 includes: a housing 11 configured to receive an empty syringe 5 and bulk fluid sources; a user interface 13 configured to allow a user to control the container loading device 3 to fill the syringes 5 and to allow entry of at least one of information related to the syringes 5, information related to at least one of an injection procedure, and information related to a patient; and an information read/write device 15 configured to: read information related to the syringes 5 stored on one or more information storage devices associated with the syringes 5; and write information related to at least one of an injection procedure and a patient to the one or more information storage devices.

In some embodiments, the user interface 13 and the information read/write device 15 may be integrally formed with the housing 11 of the container loading device 3. Alternatively, as discussed with reference to FIG. 18 hereinafter, these devices may be separate components operatively connected to the container loading device 3. In addition, some embodiments provide that the user interface 13 may be presented on a display device operatively coupled to a computing device 17. The computing device 17 may include a processing device 19 and memory 21. An exemplary computing device 17 that may be integrated into the container loading device 3 to provide the user interface 13 and other features of the container loading device is shown in FIG. 2.

Figure 2:
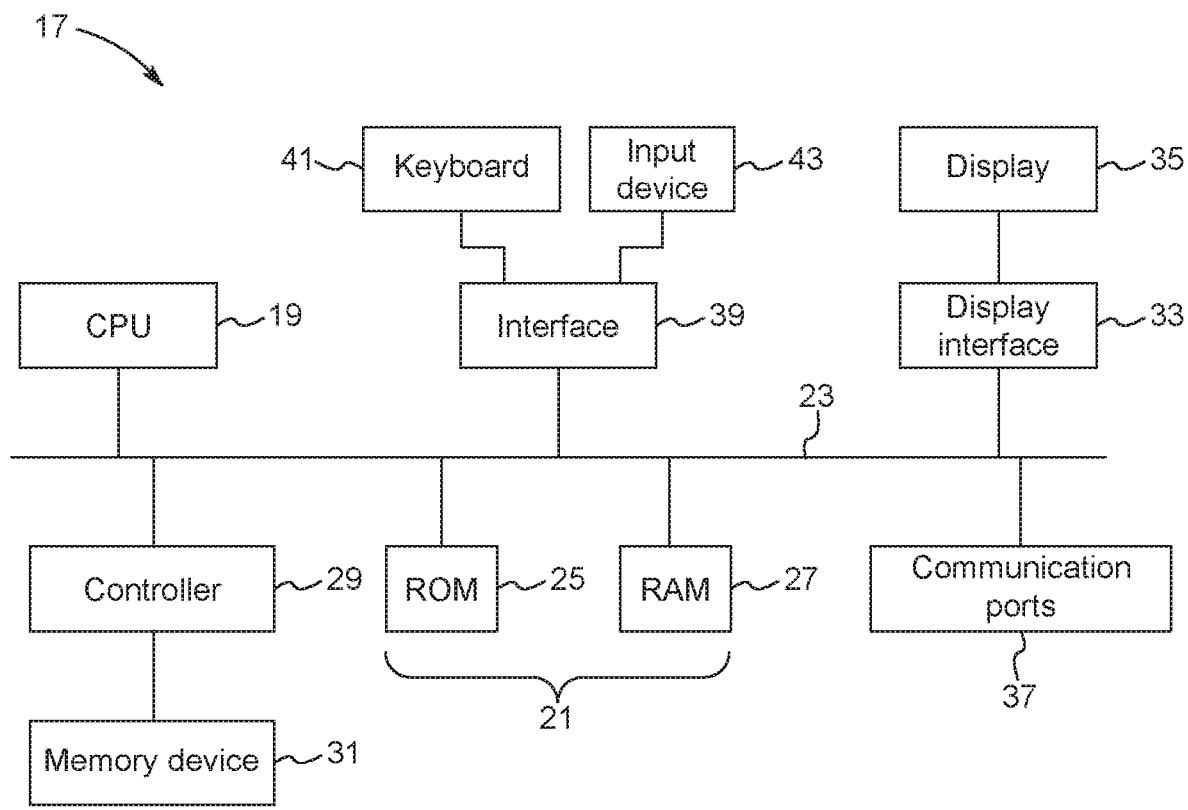
FIG. 2 is a schematic block diagram of internal hardware of a computing device in accordance with some embodiments of the present disclosure.

With reference to FIG. 2 and with continued reference to FIGS. 1A-1C, illustrative computing device internal hardware according to some embodiments that may be used to contain or implement program instructions is shown. The computing device 17 may include a bus 23 that serves as the main information highway interconnecting the other illustrated components of the hardware. CPU 19 is the central processing unit of the system, performing calculations and logic operations required to execute a program. CPU 19, alone or in conjunction with one or more of the other elements disclosed in FIG. 2, is an exemplary processing device, computing device or processor as such terms are used within this disclosure. Read only memory (ROM) 25 and random access memory (RAM) 27 constitute exemplary memory devices 21 (i.e., processor-readable non-transitory storage media).

A controller 29 interfaces with one or more optional memory devices 31 to the system bus 23. These memory devices 31 may include, for example, an external or internal DVD drive, a CD ROM drive, a hard drive, flash memory, a USB drive or the like. These various drives and controllers are optional devices.

Program instructions, software or interactive modules for providing the interface and performing any querying or analysis associated with one or more data sets may be stored in the ROM 25 and/or the RAM 27. Optionally, the program instructions may be stored on a tangible computer readable medium such as a compact disk, a digital disk, flash memory, a memory card, a USB drive, an optical disc storage medium, such as a Blu-ray™ disc, and/or other non-transitory storage media.

An optional display interface 33 may permit information from the bus 23 to be displayed on the display 35, which may be part of the user interface 13, in audio, visual, graphic, or alphanumeric format. Communication with external devices, such as a print device, which may be part of the information read/write device 15, may occur using various communication ports 37. An exemplary communication port 37 may be attached to a communications network, such as the Internet or an intranet.

The hardware may also include an interface 39 which allows for receipt of data from input devices such as a keyboard 41 or other input device 43 such as a mouse, a joystick, a touch screen, a remote control, a pointing device, a video input device and/or an audio input device. The keyboard 41 and other input devices 43 may also be part of the user interface 13.

Returning to FIGS. 1A-1C, once the empty syringes 5 and bulk fluid sources 4, 6 are provided to the housing 11 of the container loading device 3, the container loading device fills the syringes 5 with the correct amount of fluids based on information read from the information storage devices. More specifically, empty syringes 5 are attached to or loaded onto the housing 11 of the container loading device 3 and connected via tubing 8 to a bulk fluid source such as a bag 6 or a bottle 4. Each drive member (not shown) of container loading device 3 is coupled to a plunger of one of the empty syringes 5. The drive members are then actuated to draw the syringe plungers rearward within the syringes 5, thereby drawing injection fluid from the sources 4, 6 into the syringes 5 for later injection into a patient. As shown in FIG. 1C, a fluid path set 83 may be fluidly connected with the distal end of the syringes 5 for delivering medical fluid from the syringes 5 to a catheter, needle, or other fluid delivery connection (not shown) inserted into a patient at a vascular access site. The fluid path set 83 may also be primed at this point. During the filling of the syringes 5, the information read/write device 15 is configured to write information related to at least one of an injection procedure and a patient to the information storage device associated with the syringe 5.

More specifically, the container loading device 3 is configured to fill the syringes 5 with fluid based on the information related to the syringes 5 read from the one or more information storage devices by the information read/write device 5. Thereafter, the information read/write device 15 is configured to write information related to at least one of the injection procedure and the patient to the information storage device as the container loading device 3 is filling syringes 5 with fluid. As will be discussed in greater detail hereinafter, a fluid injector system is then configured to read the information related to the injection procedure and/or the patient from the information storage device when the syringes 5 are received by the fluid injector system and the information related to the injection procedure and/or the patient is then used to program the fluid injector system to conduct the injector procedure.

The information storage device may be any suitable device that may have information written thereto and read therefrom. For example, the information read/write device 15 may be configured as a radiofrequency identification (RFID) read/write device and the one or more information storage devices are RFID tags. The information related to the syringes 5 stored on the one or more information storage devices may include one or more of the following items: (i) a type of the contrast media, (ii) a concentration of the contrast media, (iii) a manufacturer of the contrast media, (iv) a lot number of the contrast media, (v) a serial number of the contrast media, (vi) a manufacturer instructions for the contrast media, (vii) a creation date of the contrast media, (viii) an expiration date of the contrast media, and (ix) a size of the one or more containers. Such information may be generated by the manufacturer or supplier of the fluid contained in the one or more containers. In addition, the information related to the injection procedure and/or the patient written to the one or more information storage devices may include one or more of the following: (i) a pressure and a flow rate for the fluid injector system, (ii) patient weight information, (iii) patient height information, (iv) patient age information, (v) patient name information, (vi) hospital information, (vii) department information, (viii) doctor information, (ix) medical procedure information, (x) medical imaging information, and (xi) automated injection information.

Alternatively, the information read/write device 15 may be configured as a barcode reader and a barcode printer and the one or more information storage devices are barcode labels. In such an example, the barcode reader reads information related to syringes 5 stored on one or more bar code labels associated with the syringes 5 and the barcode printer prints bar code labels including information related to at least one of the injection procedure and the patient.

Figure 3:
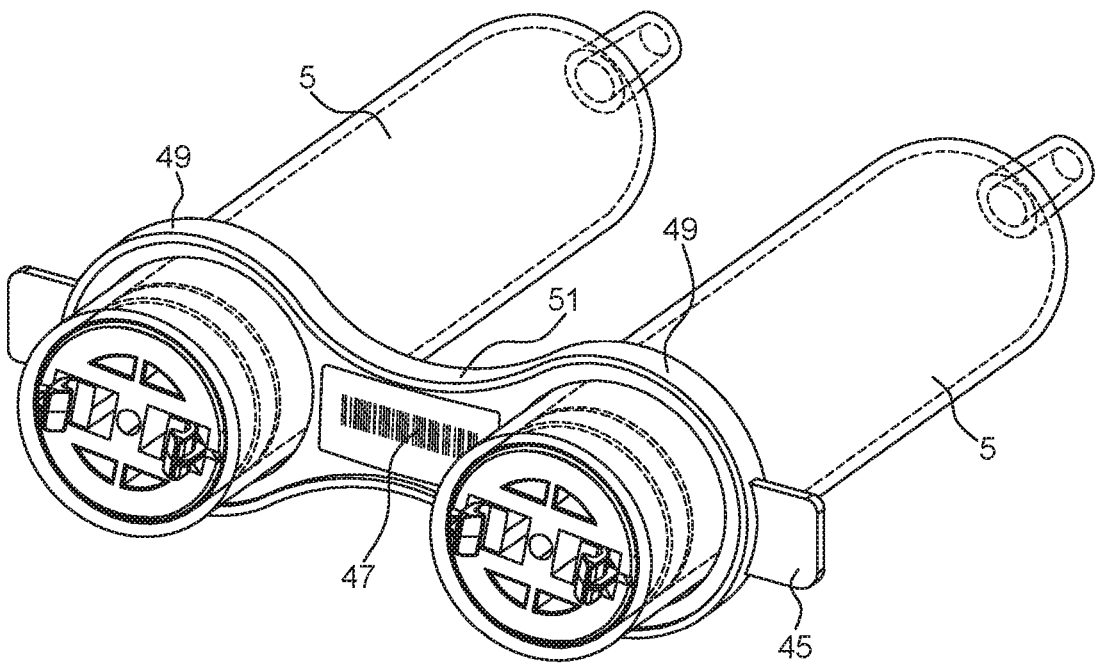
FIG. 3 is a rear perspective view of a pair of syringes connected via a collar in accordance with the present disclosure.
Figure 4:
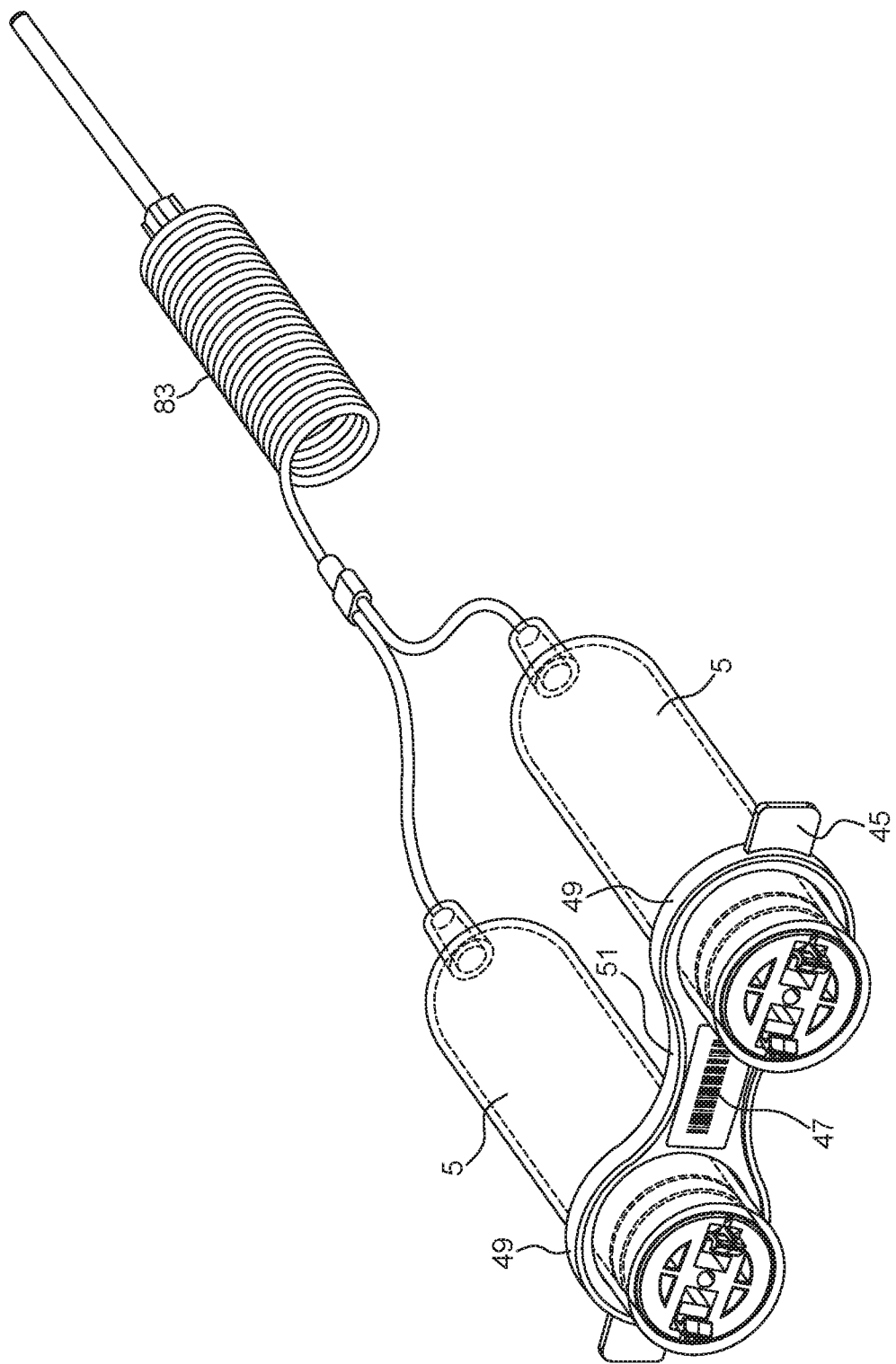
FIG. 4 is a rear perspective view of the pair of syringes of FIG. 3 having a patient tubing set connected thereto.

In a variety of instances, it may be desirable to connect the syringe 5 for contrast and the syringe 5 for saline. For example, the syringes 5 may be used in a dual-syringe fluid injector designed for the administration of two fluids such as contrast and saline. In such injection systems, the two containers of fluid disclosed herein may take the form of two syringes 5 and those syringes may be coupled together, as shown in FIGS. 1A-1C, 3, and 4, via a collar 45. The information storage device 47, which may be an RFID tag or barcode, may be removably attached or embedded within the collar 45. The collar 45 comprises a pair of openings 49 sized and shaped to engage one of the syringes 5 near the base of the syringe 5 and a body member 51 connected between the openings. In one example and as shown in FIGS. 3 and 4, the information storage device is attached to or embedded within the body member 51. In addition, the body member 51 is sized such that the syringes 5 are indexed within the injector so that they are held in the proper orientation and distance for insertion into the injector. In some examples, the information storage device 47 may be provided in a manner that is offset from the center of the body member 51. In this way, if the syringes are inserted into the fluid injector in the wrong orientation, the information storage device 47 will not be read by the information read/write deice 15, thereby providing an indication to the user that the syringes have been inserted incorrectly.

Figure 5:
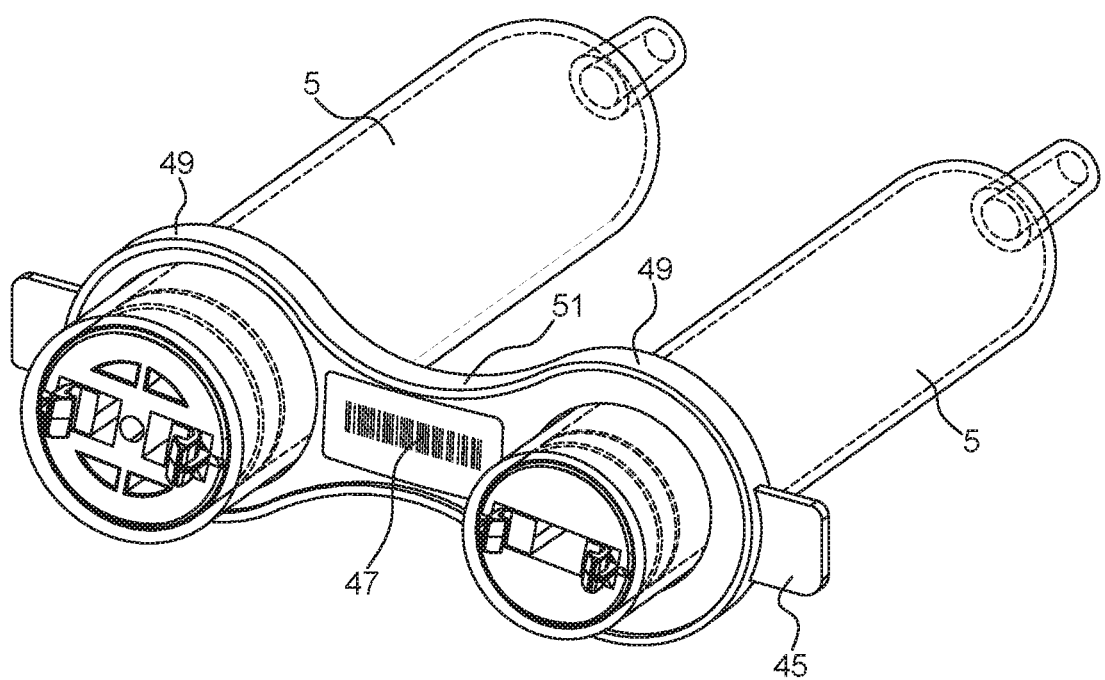
FIG. 5 is a rear perspective view of an alternative embodiment of a pair of syringes connected via a collar in accordance with the present disclosure.
Figure 6:
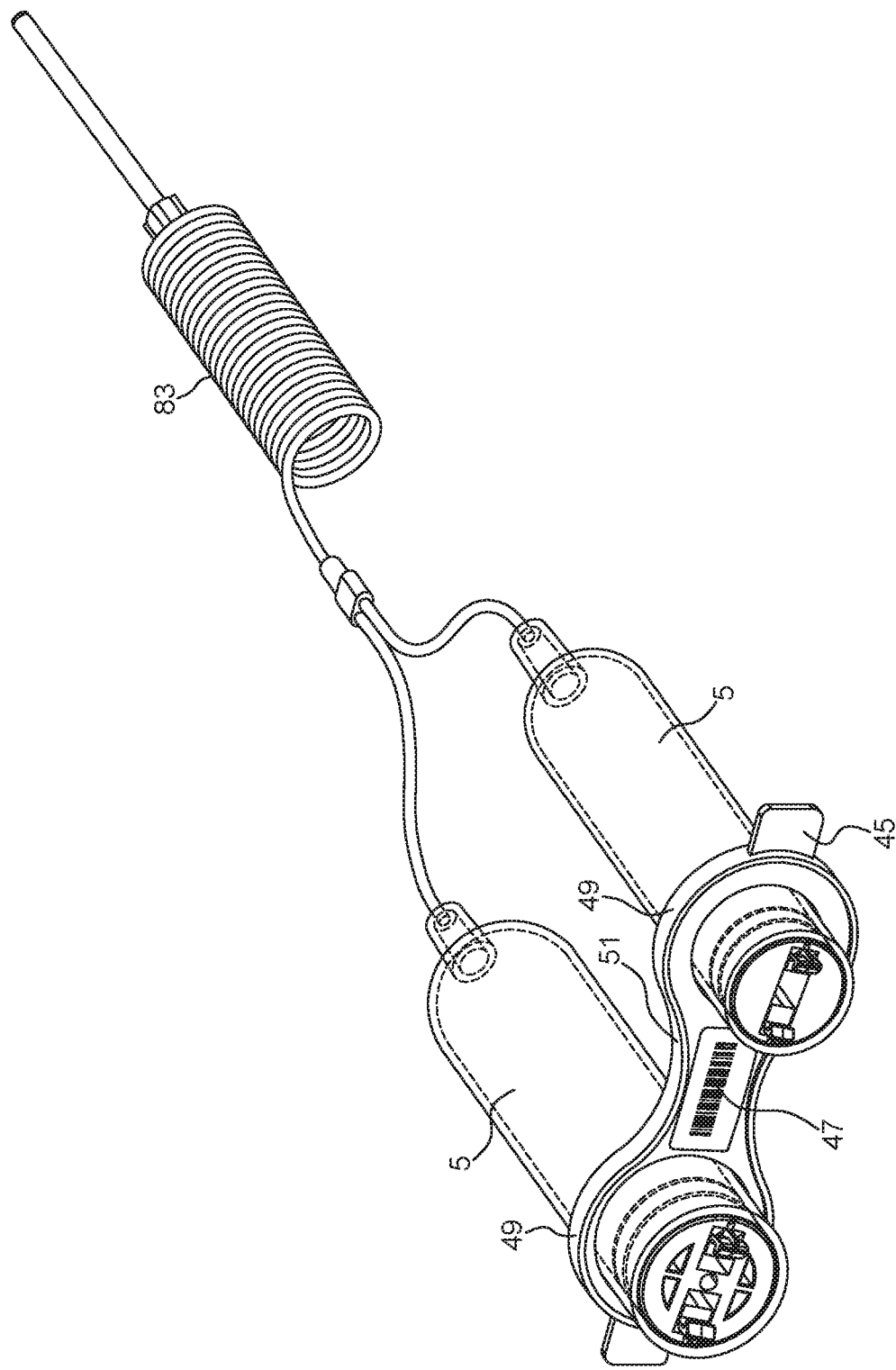
FIG. 6 is a rear perspective view of the pair of syringes of FIG. 5 having a patient tubing set connected.
Figure 7:
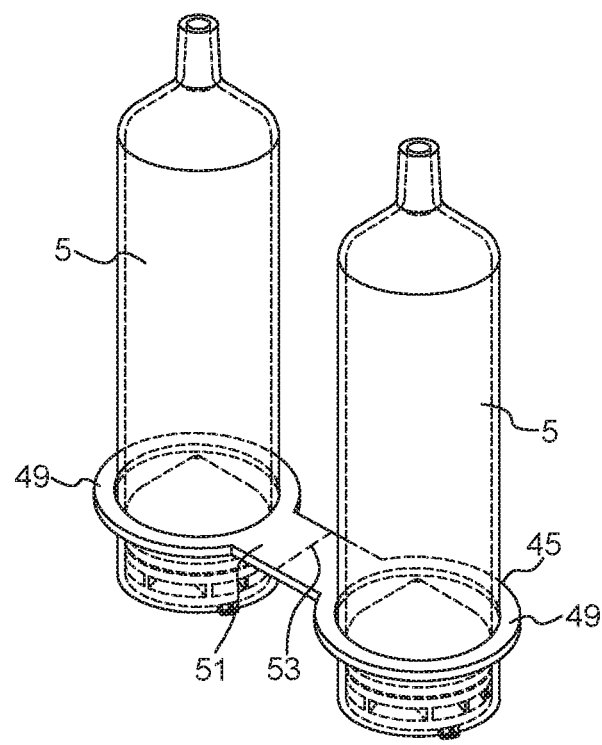
FIG. 7 is perspective view of a pair of syringes connected via a collar having a hinge with the hinge provided in an open position in accordance with the present disclosure.
Figure 8:
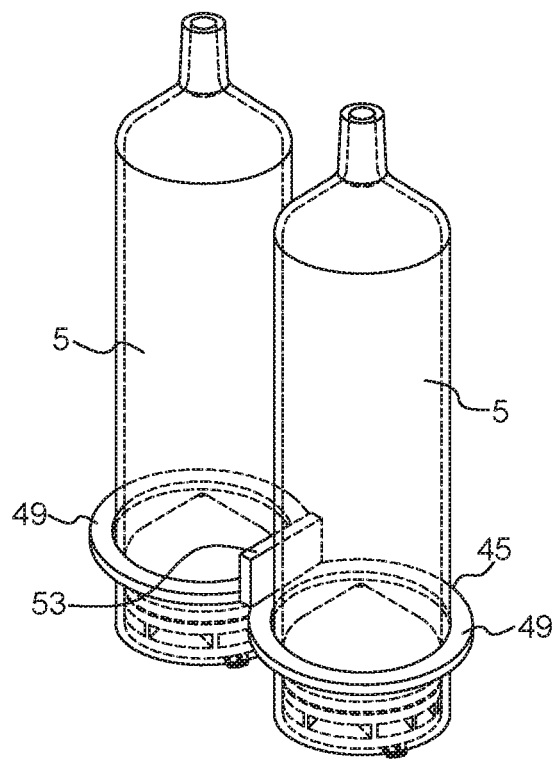
FIG. 8 is a perspective view of the pair of syringes of FIG. 7 with the hinge in the closed position in accordance with the present disclosure.

It is desirable to couple the syringes 5 when using a dual-syringe fluid injector such that the syringes 5 are indexed to the injector so that they are held in the proper orientation and distance for insertion into the injector; allow for a user to quickly and easily install the syringes 5 into and remove them from the injector, and improve workflow by requiring fewer steps for setup of the injection procedure. With reference to FIGS. 5 and 6, an alternative embodiment of the collar 45 is illustrated. This embodiment of the collar 45 is the same as the collar illustrated in FIGS. 3 and 4 in that it engages the syringes 5 near the base of the syringes 5 and includes an information storage device 47. The difference is that this collar 45 is designed to accommodate syringes of two different sizes. In addition, with reference to FIGS. 7 and 8, the body member 51 of the collar 45 may include a hinge 53, thereby allowing the syringes 5 to fold up next to each other to reduce space for shipping. While various collars 45 are illustrated in FIGS. 3-8, these collars are not to be construed as limiting the present disclosure as a variety of other collars and frames may be utilized to connect two syringes into a single component. For instance, additional frame and collar concepts that may have application in the present disclosure are also described in co-filed International Patent Application No. PCT/US2019/50340 entitled "Syringe Collar and Frame" filed simultaneously herewith on Sep. 10, 2019, which claims priority to U.S. Provisional Application Ser. No. 62/730,153 filed Sep. 12, 2018 and assigned to Bayer HealthCare LLC, each of which incorporated herein by this reference.

Figure 9:
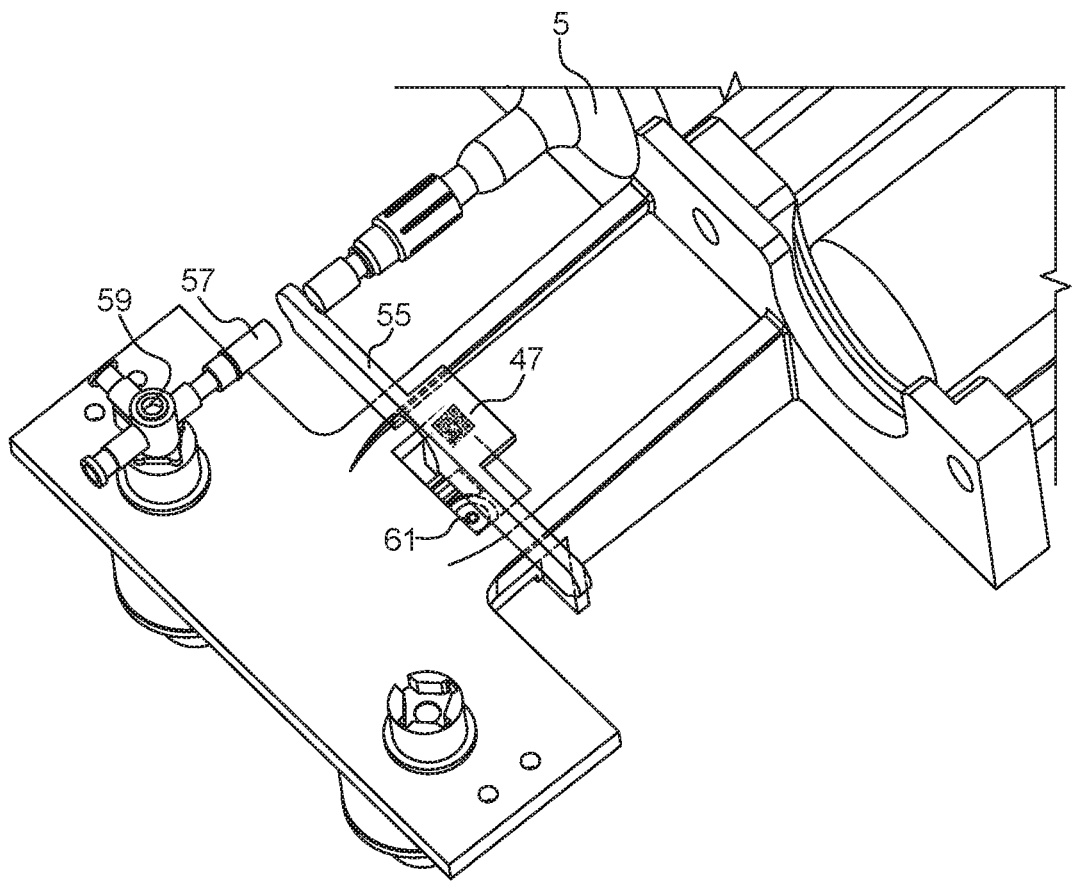
FIG. 9 is a perspective view of a portion of a fluid injection system illustrating a frame having an information read/write device in accordance with the present disclosure.
Figure 10:
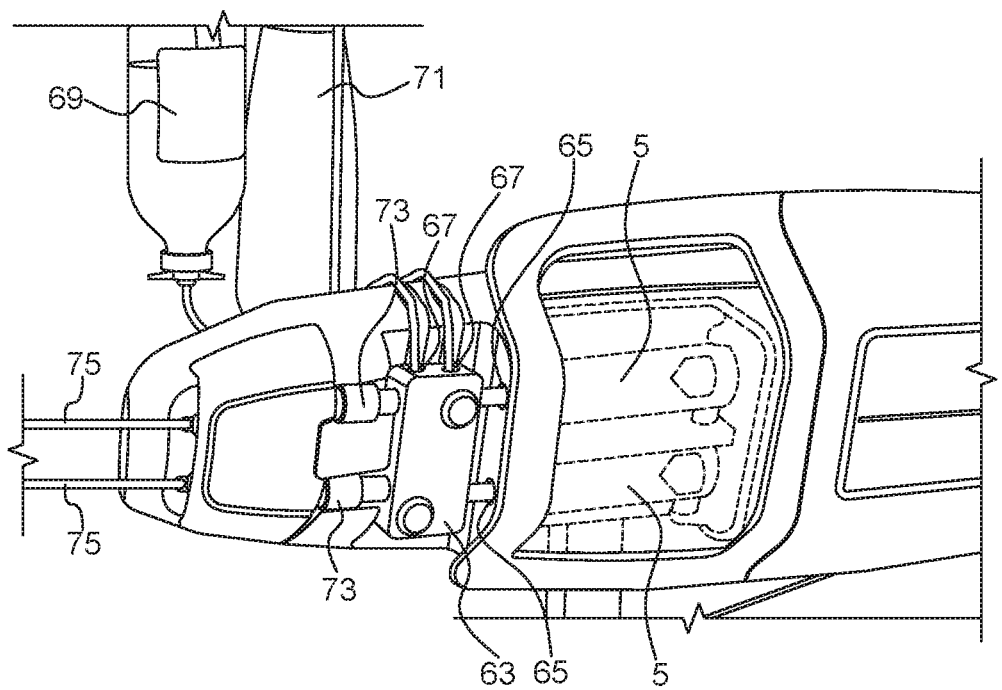
FIG. 10 is a perspective view of a portion of a fluid injection system illustrating a cartridge having an information read/write device in accordance with the present disclosure.
Figure 11:
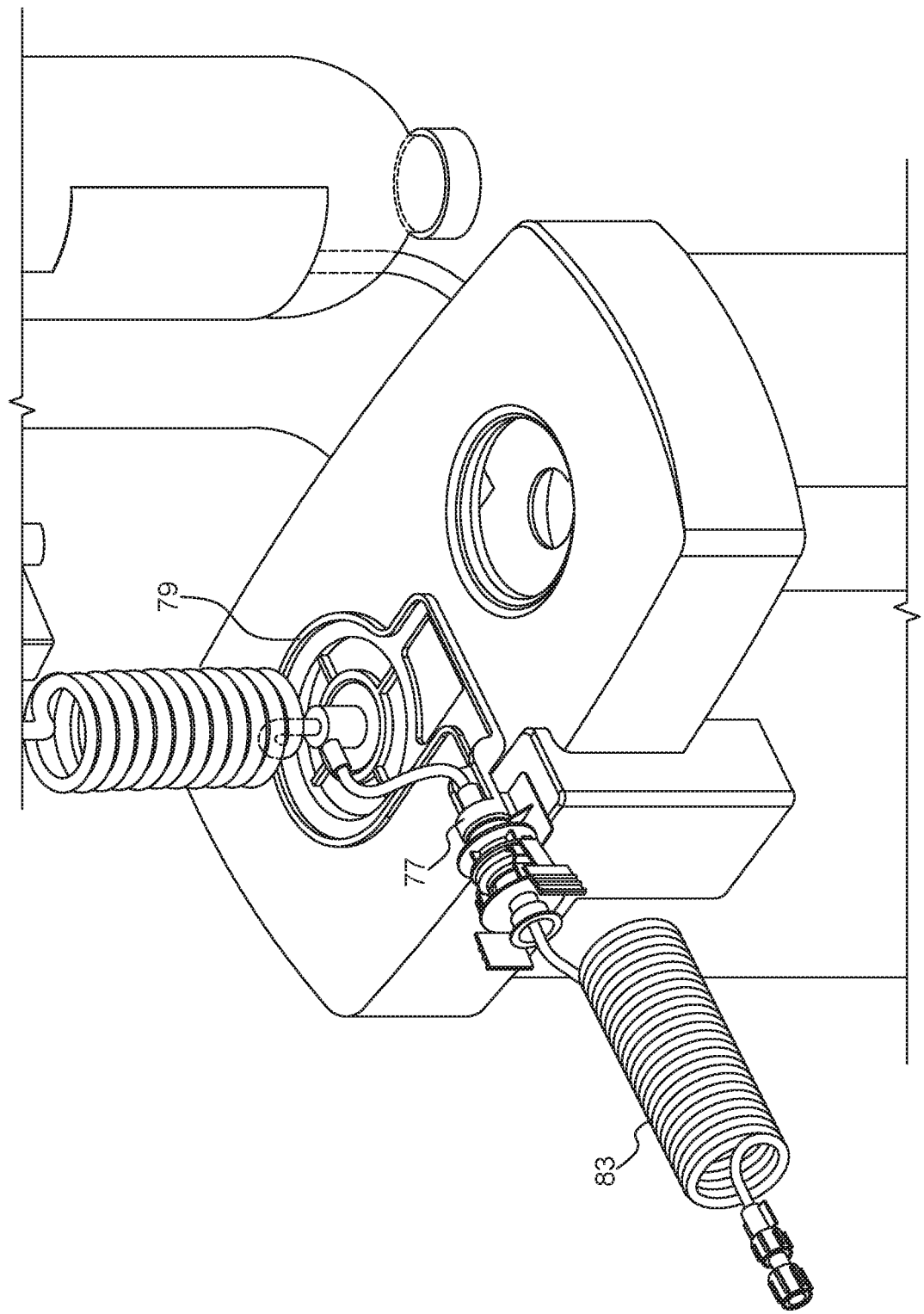
FIG. 11 is a perspective view of a portion of an alternative embodiment of a fluid injection system illustrating a frame having an information read/write device in accordance with the present disclosure.
Figure 12:
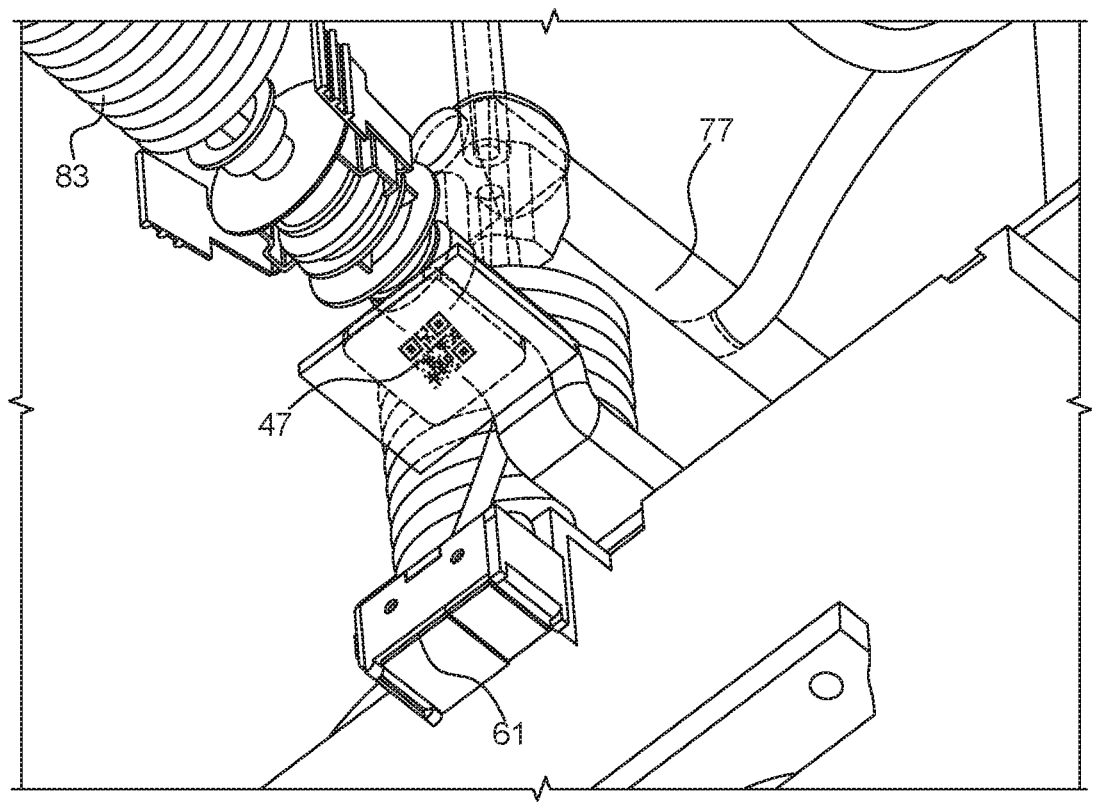
FIG. 12 is a bottom perspective view of the portion of the fluid injection system of FIG. 11.

With reference to FIGS. 9-12, in other examples of the system of the present disclosure the information storage device 47 may be incorporated into other frame structures, such as a tube management system used to manage the tubing connected to the outlet of the syringes 5. For example, and as shown in FIG. 9, a frame structure 55 is provided having the information storage device 47 incorporated therein. The frame structure 55 is designed to connect the outlets of the syringes 5 and manage any associated tubing 57 and associated valves, such as stopcock 59. Upon installation of the syringes 5 and associated frame structure 55 onto the injection system, a camera 61 provided on the injection system reads the information from the information storage device 47 and transfers the information to the injection system for use in the injection procedure to be carried out on the patient for whom the syringes 5 were prepared. With reference to FIG. 10, in an alternative example, rather than using a frame structure 55 for tube management, a cartridge 63 may be utilized. The cartridge includes inlet ports 65 configured to engage the outlets of the syringes 5, inlet ports 67 coupled to bulk fluid sources 69, 71, and a pair of outlet ports 73 configured to be connected to a suitable disposable fluid path set 75 for connection to a patient. In addition, an information storage device is incorporated or associated with the cartridge 63. Upon installation of the syringes 5 and cartridge 63 onto the injection system, a camera (not shown) provided on the injection system reads the information from the information storage device and transfers the information to the injection system for use in the injection procedure to be carried out on the patient for whom the syringes 5 were prepared. With reference to FIGS. 11 and 12, an alternative frame structure 77 may be utilized and connected between an outlet 79 of syringe 5 and a disposable fluid path set or connector tubes 83. The frame structure 77 may have an information storage device 47 associated therewith that may be read by a camera 61 associated with the injection.

Returning to FIGS. 1A-1C, any of the above described syringes 5, whether coupled via a collar or frame structure to another syringe or other structure, such as tubing, may be filled using the container loading device 3. In the example where a pair of syringes 5 are connected via the collar 45 as shown in FIG. 3, an operator can fill the two syringes with the appropriate fluids (e.g., contrast and saline) from bulk fluid sources 4, 6 in the appropriate amounts and then program information storage device 47 with both the patient data (e.g., patient name or other identifier) and the injection protocol that is to be carried out on the patient for whom the syringes are being prepared using the container loading system 3. Optionally, an identifier for the loading device being used to load the syringes as well an identifier for the operator who performed the loading operation may also be programmed into the information storage device 47. The container loading device 3 may be used to load either brand name or generic syringes with the desired fluids from bulk fluid sources. Use of such bulk fluid sources may permit the fluid(s) to be delivered to patients at a lower cost per injection. The loading device 3 also allows the operator (e.g., in an MRI suite) to fill the syringes in the control room of the imaging suite and store the requisite information (e.g., patient data and the syringe loading parameters) onto the information storage device 47.

During this loading operation, after being programmed with the requisite information, the information storage device 47 will ideally be designed so as to retain the information for at least as long as it is connected to the collar. In addition, information storage device 47 may be designed so that it automatically erases upon being removed from the collar 45 or upon removal of the collar 45 from the syringes 5. In such instances, the collar 45 and/or the information storage device 47 can be reused. When the syringes 5 are removed from the container loading device, the appropriate connector tubing or fluid path set 83 can then be attached to the syringes 5 before leaving the control room (as shown in FIG. 1C). Priming of the tubing can be done either with the loading device 3 or with the injection system.

Once the syringes 5 have been filled as described hereinabove, they are transported to the injection system to begin an injection procedure. Various examples of the present disclosure are directed to fluid injection systems for injecting one or more fluids into a patient during an injection procedure. In particular examples, the fluid injection systems of the present disclosure may be used for injection of one or more imaging agents in an imaging procedure, such as, for example, CT scan, MRI, and other radiological imaging procedures. The various examples of the fluid injection systems may comprise an injector assembly comprising at least one syringe port for interfacing with a syringe and be configured to inject one or more medical fluids during an imaging procedure.

In specific examples, the fluid injector system may be a front-loading fluid injector system similar to the various examples of the injectors disclosed in U.S. Pat. Nos. 5,383,858, 7,553,294, 7,666,169, 9,173,995, 9,199,033 and in International Patent Application Publication No. WO2016/191485, and in U.S. Patent Application Publication No. 2014/0027009, the disclosures of which are incorporated by reference in their entirety.

Figure 13A:
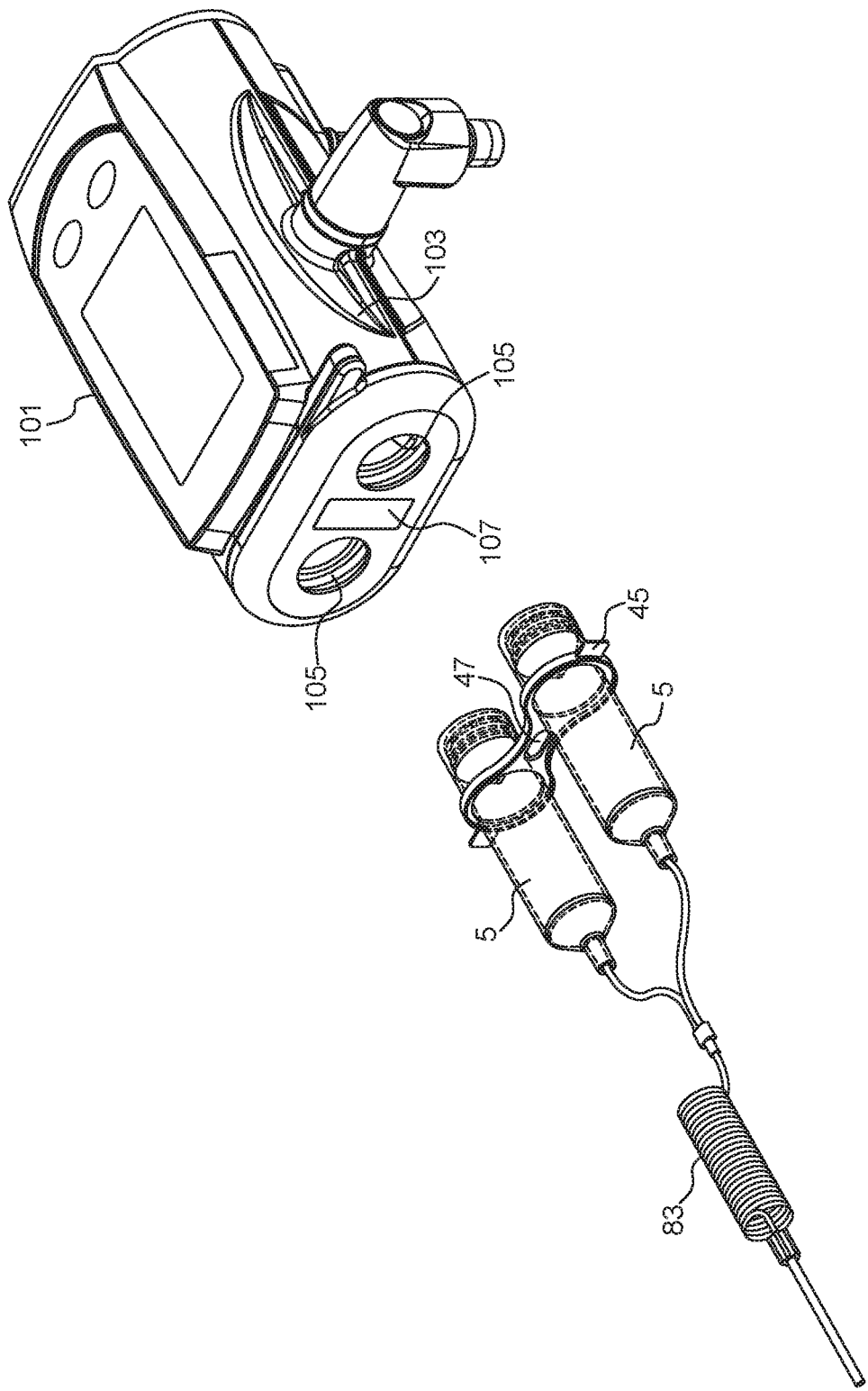
FIGS. 13A and 13B are perspective views of a fluid injection system in accordance with the present disclosure at different stages of a fluid injection procedure.
Figure 13B:
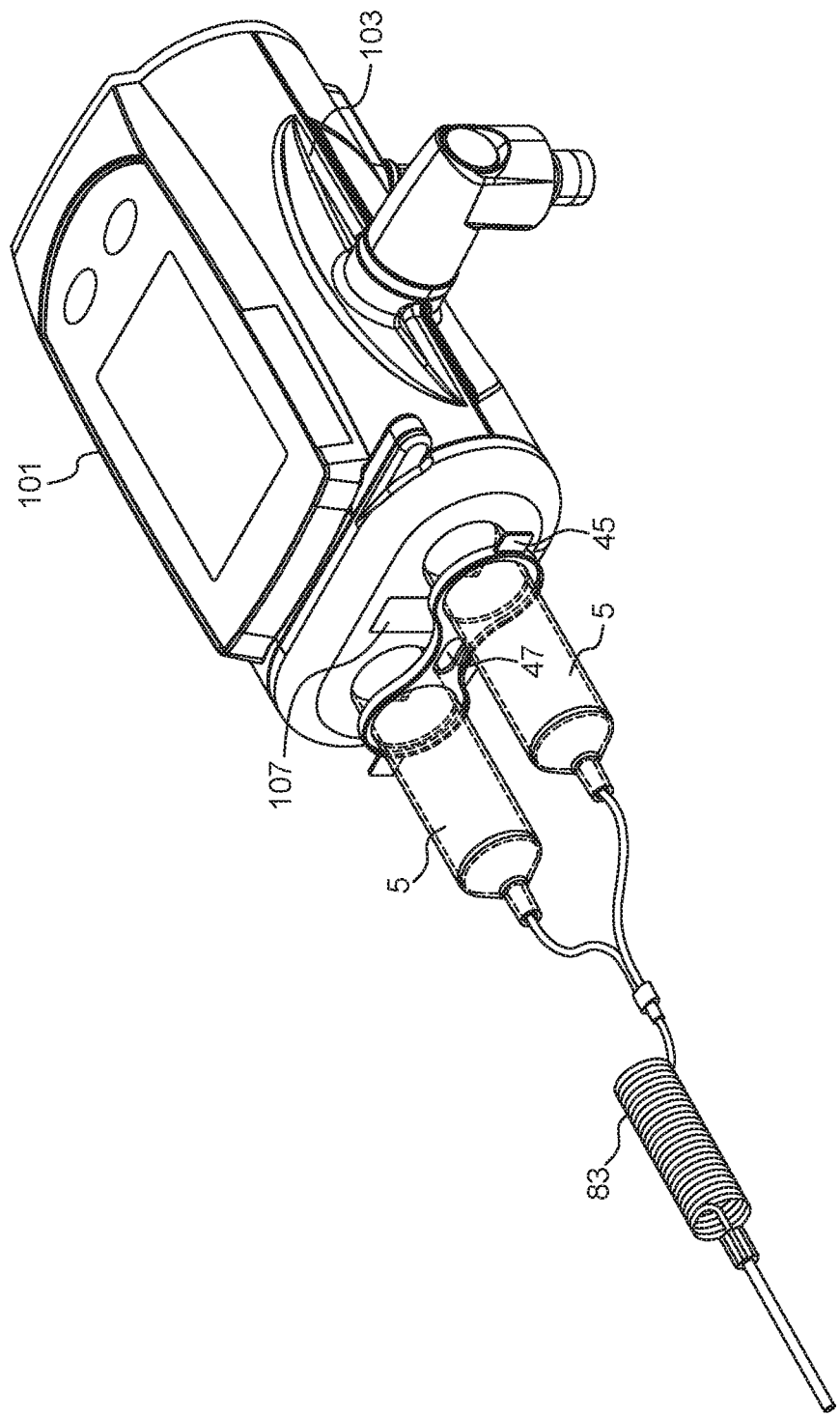

FIGS. 13A and 13B illustrate a fluid injection system 101 according to a non-limiting example of the present disclosure. With reference to FIGS. 13A and 13B, the fluid injection system (hereinafter referred to as "injector 101"), such as an automated or powered fluid injector, is adapted to interface with and actuate the syringes 5 connected via the collar 45. The syringes 5 are desirably independently filled with a medical fluid, such as contrast media having a desired concentration or identity, saline solution, or other desired medical fluids as described hereinabove. The injector 101 may be used during a medical procedure, such as an imaging procedure, to inject the medical fluid into the body of a patient by driving a plunger (not shown) of the at least one of the syringes 5 with at least one piston (not shown) operated by a fluid control device, which may be at least partially internal to the injector 101. In non-limiting examples, the injector 101 may be a multi-syringe injector, wherein the syringes 5 may be oriented side-by-side or in another arrangement and include plungers separately actuated by respective pistons associated with the injector 101, and controlled by the fluid control device. In one non-limiting example, two syringes may be arranged in a side-by-side fashion and filled with two different medical fluids, such as a contrast agent and a saline solution, and the injector 101 may be configured to deliver fluid to a patient from one or both of the syringes 5 either sequentially or simultaneously. It will be appreciated that various other arrangements are possible.

The injector 101 may have a housing 103 formed from a suitable structural material, such as plastic, a composite material, and/or metal. The housing 103 may be of various shapes and sizes depending on the desired application. For example, the injector 101 may be a freestanding structure having a support portion connected to a base with one or more rollers or wheels such that the injector 101 is movable over the floor. In other examples, the injector 101 may have smaller design for placement on a suitable table or support frame. The injector 101 may include a pair of syringe ports 105 for releasably connecting the syringes 5 to respective piston elements. In various examples, the syringes 5 each include at least one syringe retaining member (not shown) configured for retaining the syringes 5 within the respective syringe port 105 of the injector 101. In non-limiting examples, the at least one syringe retaining member is configured to operatively engage a locking mechanism provided on or in the syringe port 105 of the injector 101 to facilitate self-oriented loading and/or removal of the syringes 5 to and from the injector 101. The syringe retaining member and the locking mechanism together define a connection interface for connecting the syringes 5 to the injector 101.

In non-limiting examples, at least one fluid path set 83 may be fluidly connected with the distal end of the syringes 5 for delivering medical fluid from the syringes 5 to a catheter, needle, or other fluid delivery connection (not shown) inserted into a patient at a vascular access site. Fluid flow from the syringes 5 may be regulated by a fluid control module operated by a controller. The fluid control module may operate various, pistons, valves, and/or flow regulating devices to regulate the delivery of the medical fluid, such as saline solution and contrast, to the patient based on one or more user selected injection parameters, such as injection flow rate, duration, total injection volume, and/or ratio of contrast media and saline. In one example, the injection parameters may be automatically provided to the fluid control module when the syringes 5 are installed on the injector 101. More specifically, upon installation of the syringes 5 and associated collar 45 onto the injector 101 as best shown in FIG. 13B, the drive member (not shown) of the injector engages the plungers of the syringes 5. If the syringes 5 are installed incorrectly or if syringes of a wrong size are installed, the drive members will not be advanced to the correct position and an indication will be provided to the user that the incorrect syringes have been installed. Once the syringes 5 are correctly installed, information from the information storage device 47 may be transferred to the injector 101 by an information read device 107 for use in the injection procedure to be carried out on the patient for whom the syringes 5 were prepared. The information read device 107 may be a camera configured to read and detect a barcode, a QR code, an RFID reader, or any other suitable device depending on the information storage device 47 provided on the collar 45. Consistent with the foregoing and as discussed hereinabove, the information storage device 47 may be programmed with one or more of the following information: fluid batch number, fluid batch date, contrast type, contrast volume, saline volume, patient name or other identifier, injection protocol to be performed, and whether or not the attached tubing set 83 is primed.

Figure 14:
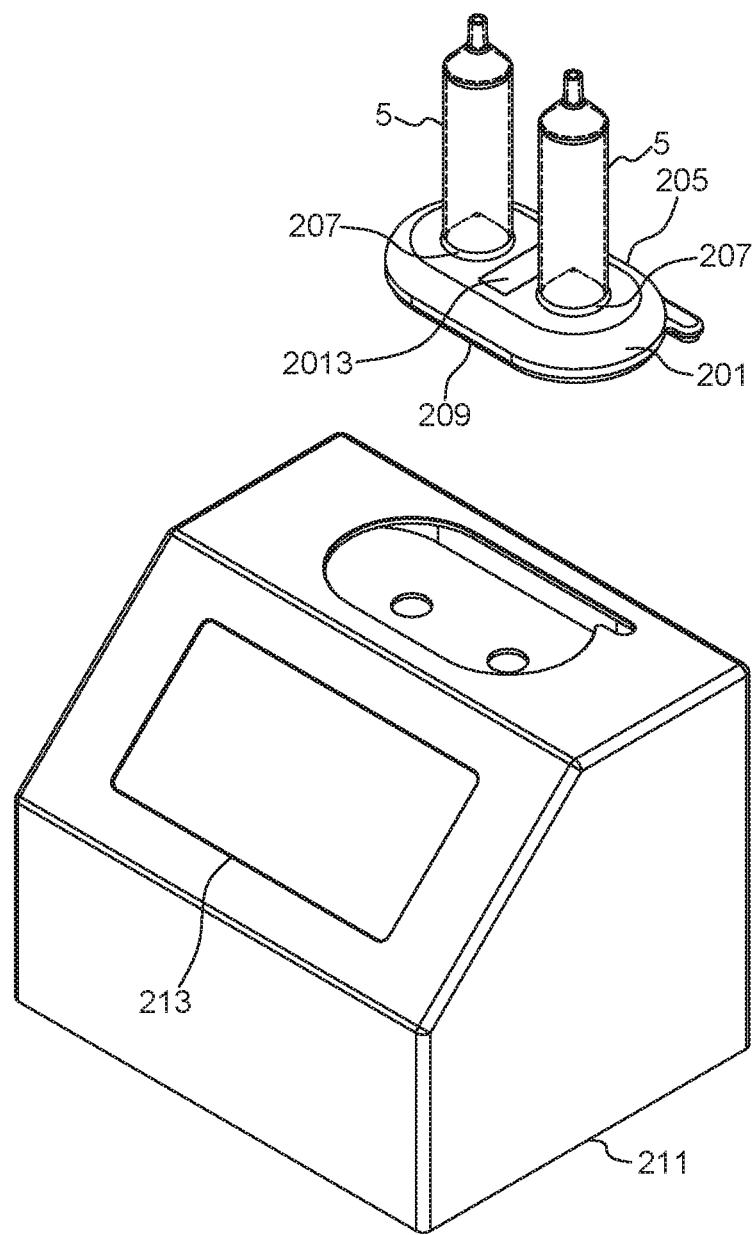
FIG. 14 is a perspective view of an alternative embodiment of a loading device prior to having a pair of syringes and faceplate connected thereto in accordance with the present disclosure.
Figure 15:
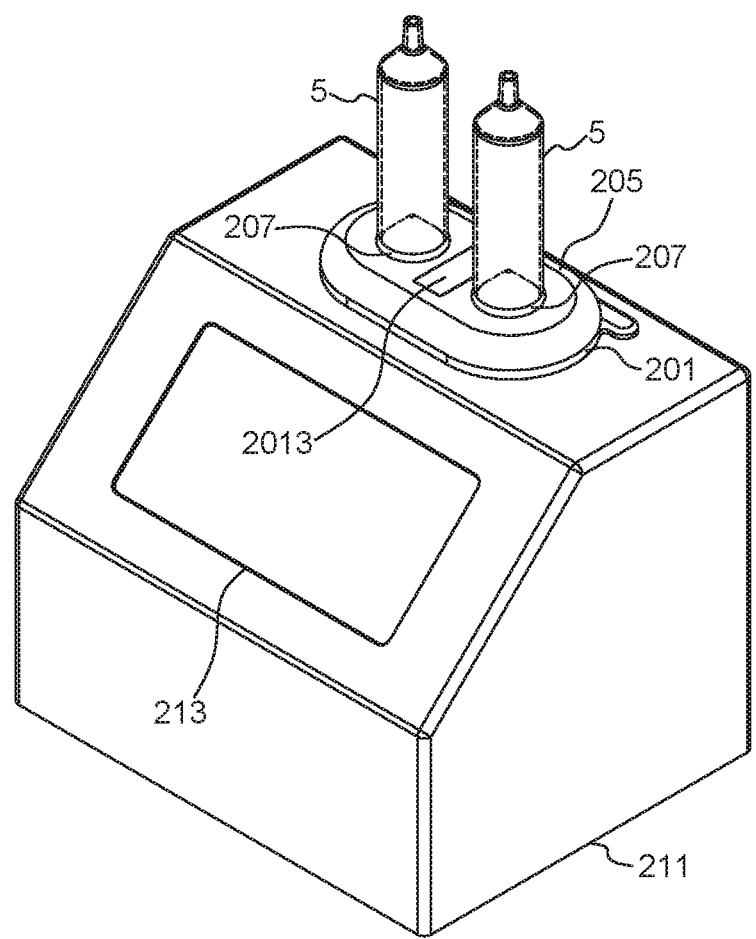
FIG. 15 is a perspective view the loading device of FIG. 14 having the pair of syringes and faceplate connected thereto.
Figure 16:
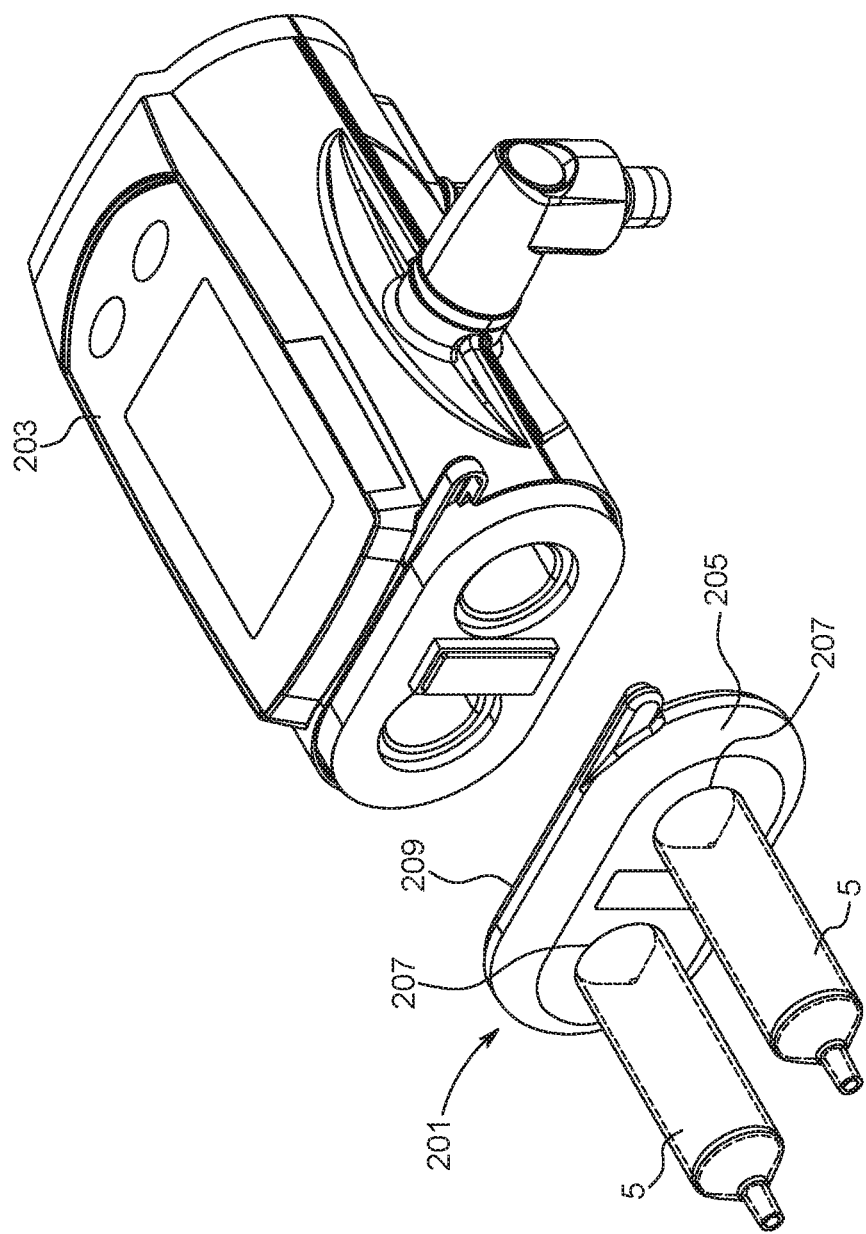
FIG. 16 is a perspective view of fluid injection system prior to having the pair of syringes and faceplate of FIG. 14 connected thereto.

With reference to FIGS. 14-16, rather than using the frames and collars as discussed hereinabove, the system of the present disclosure may also be implemented utilizing a programmable faceplate 201. The programmable faceplate 201 is part of the injector 203 and may be configured as a disposable or reusable item. The faceplate 201 includes a body portion 205 having a pair of syringe ports 207 configured to engage and removably secure each of the syringes 5 by the ends thereof. A bottom side 209 is configured to engage and removably secure the faceplate 201 to both a loading device 211 and the injector 203. In operation, the programmable faceplate 201 is loaded with two empty syringes 5. The loading device 211 is programmed using either a user interface 213 or from a control room console for the injection and the patient. Specifically, the loading device 211 may be programed with one or more of the following parameters: fluid batch number, fluid batch date, contrast type, contrast volume, saline volume, patient name or other identifier, injection protocol to be performed, and whether or not an attached tubing set will be primed. Thereafter, the faceplate 201, along with the syringes 5, is secured to the loading device 211 and the syringes 5 are filled with the appropriate fluid. At this point, a tubing set may be installed and primed. The faceplate 201 further includes electronics to record the patient information, the fill volumes, and the protocol from the loading device 211. Alternatively, the faceplate 201 may be provided with a bar code or RFID tag and the loading device 211 would be provided with a corresponding barcode printer or RFID read device to provide the above described information to the faceplate 201.

Figure 17:
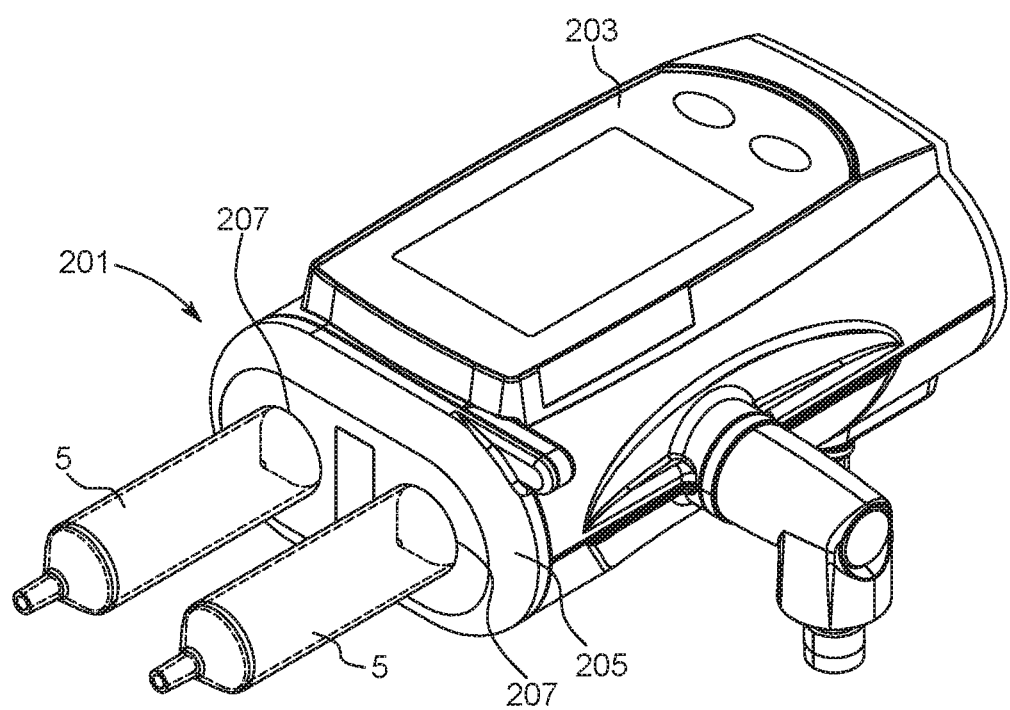
FIG. 17 is a perspective view of the fluid injection system of FIG. 16 having the pair of syringes and faceplate connected thereto.

Once the syringes are filled and the relevant information is transferred to the faceplate 201 as described above, the faceplate 201 and filled syringes 5 are moved from the loading device 211 to the injector 203 as shown in FIGS. 16 and 17. At this point, all of the information stored on the faceplate 201 is transferred to the injector 203. When the drive members are advanced to connect to the plungers, the injector 203, depending on how it is configured, may be used to verify that the correct syringes are installed by advancing each of the drive members so that each drive member engages its corresponding plunger at an expected plunger position. The injector 203, at this point, could even automatically arm itself. Configuring the injector 203 in this manner greatly reduces the amount of time that a radiologist, technologist, or other user must spend with the injector 203 in the scan room. In some examples, the faceplate 201 may include an LED display 2013 to display information regarding the patient, such as patient identification number and/or patient name, and information regarding the procedure loaded thereon.

Figure 18:
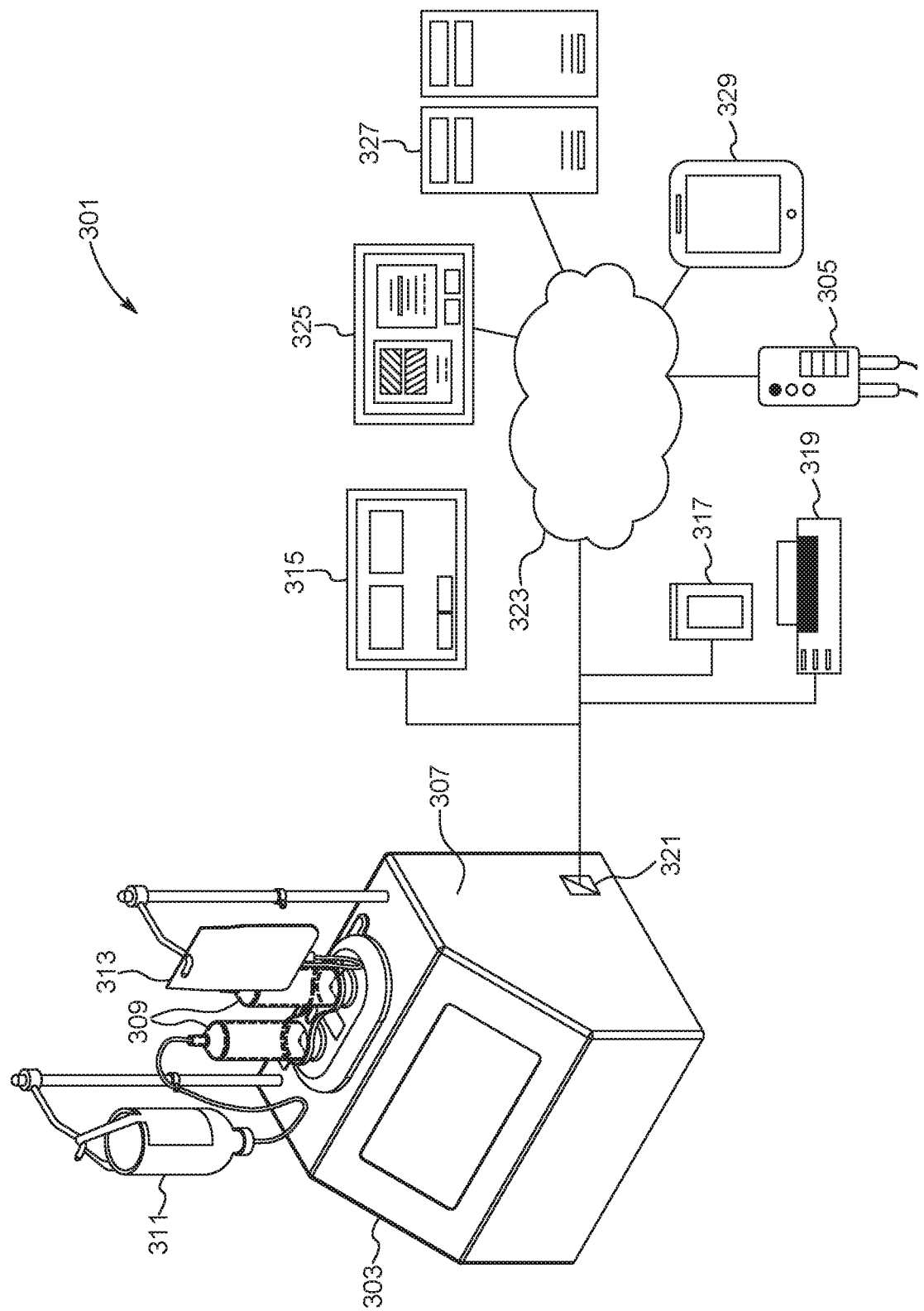
FIG. 18 is a schematic view of a system for conducting a fluid injection procedure in accordance with the present disclosure.

With reference to FIG. 18, another non-limiting embodiment or aspect of the present disclosure is directed to a system 301 for conducting a fluid injection procedure. The system 301 comprises a container loading system 303 and a fluid injector system 305.

The container loading device 303 includes: a housing 307 configured to receive at least one empty syringe 309 and bulk fluid sources 311, 313; a user interface 315 configured to allow a user to control the container loading system 303 to fill the syringes 309 and to allow entry of at least one of information related to the syringes 309, information related to at least one of an injection procedure, and information related to a patient; and an information read/write device 317 configured to: read information related to the syringes 309 stored on one or more information storage devices associated with the syringes 309; and write information related to at least one of an injection procedure and a patient to the one or more information storage devices.

The information read/write device 317 may be configured to read information associated with the syringes 309 and write information that is to be associated with the syringes 309. For example, each syringe 309 may be associated with one or more labels. Non-restrictive examples of labels include text-based, RFID, barcodes (one dimensional (1D) and/or two-dimensional (2D)), and QR codes. The information read/write device 317 may be configured to read the information associated with a corresponding type of label and thereafter write information to the label. For instance, information read/write device 317 may include an RFID read/write device configured to read RFID labels and then write information to the labels. In another instance, the information read/write device 317 may include an OCR reader configured to scan text-based labels and provide text information to one or more information consumers (e.g., the user interface 315). The information read/write device 317 may further include one or more printers 319 configured to generate labels including barcodes or QR codes to affix to the syringes 309. Some embodiments provide that information read by the information read/write device 317 may be transmitted within the system 301. For example, the information from a syringe 309 for use by a patient having a diagnostic imaging exam may be sent to the user interface 315, a PACS system, and to the fluid injector 305 that will be used to inject the contrast into the patient. In general, information obtained by the information read/write device 317 may be generally available for transmission within the system 301 to electronic devices and computing devices configured to receive and handle the information.

In some embodiments, the user interface 315, the information read/write device 317, and the printer 319 may be integrally formed with the housing 307 of the container loading system 303. Alternatively, as shown in FIG. 18, these devices may be separate components operatively connected to the container loading system 303. The user interface 315, the information read/write device 317, and the printer 319 together may be considered a data entry system associated with the loading system 303. Such a data entry system is configured to allow entry of at least one of (i) information related to the syringes 309, (ii) information related to an injection procedure, and (iii) information related to a patient.

The loading system 303 further includes a controller that is operatively connected thereto and to the data entry system. The controller may be any suitable processing device as discussed hereinabove with reference to FIG. 2. The controller is configured to receive at least one of (i) the information related to the syringes 309, (ii) the information related to the injection procedure, and (iii) the information related to the patient and to associate at least one of the (i) information related to the syringes 309, (ii) the information related to the injection procedure, and (iii) the information related to the patient with the syringes 309 as the loading device is filling the one or more containers with fluid. This information is associated with the syringes 309 as the loading system 303 is filling the syringes 309 with fluid by assigning the syringes 309 a unique code that can be entered into the fluid injector system 305. Alternatively, this information may be associated with the syringes 309 by storing the information on a data storage device associated with the syringes 309 such that the data storage device is read by the fluid injector system 305 when the syringes 309 are mounted thereto. As discussed hereinabove, the data storage device may be any suitable data storage device such as, but not limited to, an RFID tag or a barcode label.

The information related to the syringes 309 may be any one or combination of the following items: (i) a type of the contrast media, (ii) a concentration of the contrast media, (iii) a manufacturer of the contrast media, (iv) a lot number of the contrast media, (v) a serial number of the contrast media, (vi) a manufacturer instructions for the contrast media, (vii) a creation date of the contrast media, (viii) an expiration date of the contrast media, and (ix) a size of the one or more containers. In addition, the information related to the syringes 309 may be generated by the manufacturer or supplier of the fluid contained in the syringes 309.

The information related to the injection procedure and information related to the patient may be any one or combination of the following items: (i) a pressure and a flow rate for the fluid injector system, (ii) patient weight information, (iii) patient height information, (iv) patient age information, (v) patient name information, (vi) hospital information, (vii) department information, (viii) doctor information, (ix) medical procedure information, (x) medical imaging information, and (xi) automated injection information.

The loading system 303 may further include a communication device 321 that is operatively connected to the controller and is configured to transmit at least one of (i) the information related to the syringes 309, (ii) the information related to the injection procedure, and (iii) the information related to the patient. The communication device 321 may be provided within the housing 307 of the loading system 303 as shown in FIG. 18 or may be provided externally of the loading system 303. The communication device 321 may include at least one communication port configured to be connected to one or more networks 323 according to known communication methods. Illustrative and non-limiting examples of communication methods available to the communication device 321 include Ethernet, wireless protocols (e.g., IEEE 802.11g, (WiFi 3), IEEE 802.11n (WiFi 4), IEEE 802.11ac (WiFi 5), IEEE 802.11ax (WiFi 6), etc.) serial, universal serial bus (USB), parallel port, Bluetooth®, and proprietary device protocols As shown in FIG. 18, the loading system 303 may be in communication, via the communication device 321, with a network 323, including, without limitation, a local area network (LAN), wide area network (WAN), wireless network, and combinations thereof. One or more computing devices may also be connected to the network 323. Illustrative and non-restrictive examples of computing devices may include personal computing devices 325 (e.g., workstations), servers 327 (e.g., data servers, web servers, distributed computing systems (e.g., cloud computing systems), and information systems), mobile computing devices 329 (e.g., tablet computing devices and smart phones), and the fluid injector system 305.

The fluid injector system 305 is configured to: receive at least one of (i) the information related to the syringes, (ii) the information related to at least one of the injection procedure, and (iii) the information related to the patient from the communication device; and to associate at least one of (i) the information related to the one or more containers, (ii) the information related to at least one of the injection procedure, and (iii) the information related to the patient with the one or more containers when the one or more containers are mounted to the fluid injector system. Based on this information, the fluid injector system 305 is armed and a fluid injection procedure may then be conducted.

According to some embodiments, the servers 327 may be part of one or more information systems including, but not limited to, a picture archiving and communication system (PACS), healthcare information and management systems (HIMS), electronic medical record (EMR) systems, radiology information systems (RIS), laboratory information systems (LIS), contrast information management systems, and medical imaging and procedure equipment information systems (e.g., contrast injector systems). Some embodiments provide that the loading device, the network, and/or other information systems may be in communication with various other information platforms, such as the Certegra® Workstation offered by Bayer Healthcare. Such features allow, for example, protocol management and the generation of injection protocols using any of the Certegra® P3T software modules. For example, when used with injection systems such as the MEDRAD® Stellant CT Injection System offered by Bayer, the P3T® Cardiac, P3T® Abdomen and P3T® Pulmonary Angiography modules allow Radiologists to personalize the injection protocols for CT cardiac, pulmonary, and abdomen (liver, pancreas, and kidneys) studies, respectively. In addition to its contrast dose management capabilities, the Certegra® Workstation also enables interaction with the Modality Worklist functionality of various OEM scanners and, via its Manage.Report and Connect.PACS capabilities, transfer of injection protocol and other data to hospital IT systems including the PACS, HIMS, RIS, LIS, EMR, and the speech reporting systems used by Radiologists.

The personal computing devices 325 and mobile computing devices 329 may be used to access information and to perform functions within the loading system 303. For example, a personal computing device 325 may be configured to access a user interface (e.g., similar to the user interface 315) to access information and to perform functions associated with the loading device 303. In this manner, users may remotely access the loading system 303 and/or the user interface 315 associated therewith.

While specific embodiments of the present invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the device of the present disclosure which is to be given the full breadth of the claims appended and any and all equivalents thereof.

The invention claimed is:

1. A system for conducting a fluid injection procedure, the system comprising:
   (a) a container loading system comprising a loading device for filling one or more containers with fluid;
   (b) an information read/write device operatively associated with the loading device and configured to: read information related to the one or more containers stored on one or more information storage devices associated with the one or more containers; and write information related to at least one of an injection procedure and a patient to the one or more information storage devices; and
   (c) a fluid injector system operatively associated with the information read/write device and configured to receive the one or more containers after filling by the container loading system and inject contents of the one or more containers of the fluid into the patient;
   wherein (i) the loading device is configured to fill the one or more containers with the fluid based on the information related to the one or more containers read from the one or more information storage devices by the information read/write device; (ii) the information read/write device is configured to write the information related to at least one of the injection procedure and the patient to the one or more information storage devices as the loading device is filling the one or more containers with the fluid; and (iii) the fluid injector system is configured to read the information related to the at least one of the injection procedure and the patient from the one or more information storage devices when the one or more containers are received by the fluid injector system and the information related to the at least one of the injection procedure and the patient is used to program the fluid injector system to conduct the injection procedure,
   wherein the one or more containers of the fluid comprise at least two containers of the fluid coupled together via a structure, and the one or more information storage devices are provided on the structure, and
   that removal of the at least two containers from the structure removes information stored on the one or more information storage devices, thereby allowing the structure to be reused.

2. The system of claim 1, wherein the at least two containers of the fluid include a container of contrast media and a container of saline.

3. The system of claim 2, wherein the structure coupling the at least two containers of the fluid together is a collar coupling the container of the contrast media and the container of the saline together; and
   wherein the one or more information storage devices are provided on the collar, thereby allowing the collar to be reused.

4. The system of claim 2, wherein the structure coupling the at least two containers of the fluid together is a faceplate coupling the container of the contrast media and the container of the saline together.

5. The system of claim 4, wherein the faceplate is configured to removably engage both the container loading system and the fluid injector system.

6. The system of claim 4, wherein the one or more information storage devices are provided in the faceplate.

7. The system of claim 4, wherein the faceplate comprises a display device for displaying at least one of: information regarding the patient and information regarding the fluid injection procedure.

8. The system of claim 2, wherein the information related to the one or more containers stored on the one or more information storage devices comprises at least one of the following items: (i) a type of the contrast media; (ii) a concentration of the contrast media; (iii) a manufacturer of the contrast media; (iv) a lot number of the contrast media; (v) a serial number of the contrast media; (vi) a manufacturer instructions for the contrast media; (vii) a creation date of the contrast media; (viii) an expiration date of the contrast media; and (ix) a size of the one or more containers.

9. The system of claim 8 wherein the information related to the one or more containers stored on the one or more information storage devices is generated by the manufacturer or supplier of the fluid contained in the one or more containers.

10. The system of claim 1, wherein the information read/write device is an RFID read/write device and the one or more information storage devices are RFID tags.

11. The system of claim 1, wherein the information related to the at least one of the injection procedure and the patient written to the one or more information storage devices comprises at least one of: (i) a pressure and a flow rate to be used by the fluid injector system; (ii) patient weight information; (iii) patient height information; (iv) patient age information; (v) patient name information; (vi) hospital information; (vii) department information; (viii) doctor information; (ix) medical procedure information; (x) medical imaging information; and (xi) automated injection information.

12. The system of claim 1, wherein the information read/write device is a barcode reader and a barcode printer and the one or more information storage devices are barcode labels.

13. The system of claim 12, wherein the barcode reader reads the information related to the one or more containers stored on one or more barcode labels associated with the one or more containers; and the barcode printer prints the barcode labels including the information related to at least one of the injection procedure and the patient.

14. A system for conducting a fluid injection procedure, the system comprising:
   (a) a container loading system comprising a loading device for filling one or more containers with fluid, the one or more containers including one or more information storage devices associated therewith;
   (b) a data entry system associated with the loading device and configured to allow entry of at least one of information related to the one or more containers; information related to at least one of an injection procedure; and information related to a patient;
   (c) a controller operatively connected to the loading device and the data entry system and configured to receive at least one of the information related to the one or more containers, the information related to at least one of the injection procedure and the information related to the patient and associate at least one of the information related to the one or more containers, the information related to at least one of the injection procedure and the information related to the patient with the one or more information storage devices as the loading device is filling the one or more containers with fluid;
   (d) a communication device operatively connected to the controller and configured to transmit at least one of the information related to the one or more containers, the information related to at least one of the injection procedure and the information related to the patient;
   (e) a fluid injector system configured to: receive at least one of the information related to the one or more containers, the information related to at least one of the injection procedure and the information related to the patient from the communication device and associate at least one of the information related to the one or more containers, the information related to at least one of the injection procedure and the information related to the patient with the one or more information storage devices when the one or more containers are mounted to the fluid injector system; and
   wherein the one or more containers comprise at least two containers of the fluid coupled together via a structure, and the one or more information storage devices are provided on the structure, and
   that removal of the at least two containers from the structure removes information stored on the one or more information storage devices, thereby allowing the structure to be reused.

15. The system of claim 14, wherein at least one of the information related to the one or more containers, the information related to at least one of the injection procedure and the information related to the patient is associated with the one or more information storage devices as the loading device is filling the one or more containers with the fluid by at least one of: assigning the one or more containers with a unique code that can be entered into the fluid injector system; and storing at least one of the information related to the one or more containers, the information related to at least one of the injection procedure and the information related to the patient on the one or more information storage devices provided on the one or more containers.

16. The system of claim 15, wherein the one or more information storage devices comprise one of an RFID tag and a barcode label.

17. The system of claim 14, wherein the information related to the injection procedure and the information related to the patient comprises at least one of: (i) a pressure and a flow rate for the fluid injector system; (ii) patient weight information; (iii) patient height information; (iv) patient age information; (v) patient name information; (vi) hospital information; (vii) department information; (viii) doctor information; (ix) medical procedure information; (x) medical imaging information; and (xi) automated injection information.

18. The system of claim 14, wherein the one or more containers of the fluid includes a container of contrast media and a container of saline.

19. The system of claim 18, wherein the information related to the one or more containers comprises at least one of the following items: (i) a type of contrast media; (ii) a concentration of the contrast media; (iii) a manufacturer of the contrast media; (iv) a lot number of the contrast media; (v) a serial number of the contrast media; (vi) a manufacturer instructions for the contrast media; (vii) a creation date of the contrast media; (viii) an expiration date of the contrast media; and (ix) a size of the one or more containers.

20. The system of claim 19, wherein the information related to the one or more containers is generated by the manufacturer or supplier of the fluid contained in the one or more containers.

21. The system of claim 14, wherein the communication device comprises a communication port configured to provide one or more communication methods selected from the group consisting of: Ethernet, wireless protocols, serial, universal serial bus (USB), and parallel port.

22. The system of claim 14, wherein the communication device is configured to transmit at least one of the information related to the one or more containers, the information related to at least one of the injection procedure and the information related to the patient to one or more of: a personal computing device; a server; a distributed computing system; a mobile computing device; a picture archiving and communication system (PACS); a healthcare information and management systems (HIMS); an electronic medical record (EMR) system; a radiology information system (RIS); and a contrast information management system.

* * * * *

UNITED STATES PATENT AND TRADEMARK OFFICE
CERTIFICATE OF CORRECTION

| | | |
|---|---|---|
| PATENT NO. | : 12,119,099 B2 | Page 1 of 1 |
| APPLICATION NO. | : 17/270886 | |
| DATED | : October 15, 2024 | |
| INVENTOR(S) | : Cowan et al. | |

It is certified that error appears in the above-identified patent and that said Letters Patent is hereby corrected as shown below:

In the Specification

In Column 4, Line 41, delete "information" and insert -- information. --, therefor.
In Column 8, Line 3, delete "FIGS. 1A-IC" and insert -- FIGS. 1A-1C --, therefor.
In Column 8, Line 45, delete "view the" and insert -- view of the --, therefor.
In Column 9, Line 38, delete "relates" and insert -- relates to --, therefor.
In Column 12, Line 37, delete "deice" and insert -- device --, therefor.
In Column 12, Line 67, delete "incorporated" and insert -- is incorporated --, therefor.
In Column 18, Line 24, delete "protocols" and insert -- protocols. --, therefor.

Signed and Sealed this
First Day of April, 2025

Coke Morgan Stewart
*Acting Director of the United States Patent and Trademark Office*